US008235916B2

(12) United States Patent
Whiting et al.

(10) Patent No.: US 8,235,916 B2
(45) Date of Patent: Aug. 7, 2012

(54) SYSTEM AND METHOD FOR MANIPULATING INSERTION PATHWAYS FOR ACCESSING TARGET SITES

(75) Inventors: James S. Whiting, Los Angeles, CA (US); Neal L. Eigler, Malibu, CA (US); Brian M. Mann, Edgartown, MA (US); Werner Hafelfinger, Thousand Oaks, CA (US)

(73) Assignee: Pacesetter, Inc., Sylmar, CA (US)

( * ) Notice: Subject to any disclaimer, the term of this patent is extended or adjusted under 35 U.S.C. 154(b) by 0 days.

(21) Appl. No.: 13/248,922

(22) Filed: Sep. 29, 2011

(65) Prior Publication Data

US 2012/0035590 A1 Feb. 9, 2012

Related U.S. Application Data

(63) Continuation of application No. 11/622,654, filed on Jan. 12, 2007, now abandoned.

(60) Provisional application No. 60/764,878, filed on Feb. 3, 2006.

(51) Int. Cl.
| A61B 5/00 | (2006.01) |
| A61B 19/00 | (2006.01) |
| A61M 31/00 | (2006.01) |
| A61M 37/00 | (2006.01) |
| A61M 1/00 | (2006.01) |

(52) U.S. Cl. .................. 600/585; 128/898; 604/93.01; 604/27; 604/500

(58) Field of Classification Search .................. 600/585; 604/93.01–288.04, 523, 27, 500; 128/898
See application file for complete search history.

(56) References Cited

U.S. PATENT DOCUMENTS

| 5,282,479 | A | 2/1994 | Havran |
| 6,379,319 | B1 | 4/2002 | Garibotto et al. |
| 6,711,436 | B1* | 3/2004 | Duhaylongsod .................. 607/9 |
| 6,761,733 | B2 | 7/2004 | Chobotov et al. |
| 2003/0191448 | A1* | 10/2003 | Swindle ........................ 604/509 |
| 2009/0112050 | A1* | 4/2009 | Farnan et al. .................... 600/16 |

OTHER PUBLICATIONS

Cowley, Collin G. MD et al., "Snare-Assisted Vascular Access: A New Technique," Cath. Cardiovasc. Intervent. 1999;47:315-318.
Cribier, Alain MD et al., "Percutaneous Transcatheter Implantation of an Aortic Valve Prosthesis for Calcific Aortic Stenosis—First Human Case Description," Circulation. 2002;106:3006-3008.
Duong, Michael H. MD et al., "An Unusual Complication During Central Venous Catheter Placement," Journal of Clinical Anesthesia. 2001;13:131-132.

(Continued)

*Primary Examiner* — Max Hindenburg
*Assistant Examiner* — John Pani

(57) ABSTRACT

A method for accessing a target site in the body by transferring a guidewire from an initial insertion site on the body to a different insertion site on the body is provided. In one aspect, a method for transferring a medical device or component, such as a sensor lead, from an initial insertion site to another insertion site is also provided. A guidewire of sufficient length, pliancy and deformability to perform a transfer from one insertion site to another insertion site is provided. In one aspect, the guidewire comprises a removable core mandrel to increase rigidity, facilitate insertion and/or improve steerability. A kit or system, comprising introducers, guidewires and catheters for performing a guidewire or device transfer is also provided.

13 Claims, 23 Drawing Sheets

OTHER PUBLICATIONS

Eltchaninoff, Helene MD et al., "Percutaneous Implantation of Aortic Valve Prosthesis in Patients with Calcific Aortic Stenosis: Technical Aspects," J Interven Cardiol. 2003;16:515-521.

Piechaud, Jean-Francois MD, "Percutaneous Closure of Mitral Paravalvular Leak," J Interven Cardiol. 2003;16(2):153-155.

NonFinal Office Action, mailed Apr. 22, 2010—U.S. Appl. No. 11/622,654.

Final Office Action, mailed Oct. 7, 2010—U.S. Appl. No. 11/622,654.

NonFinal Office Action, mailed Feb. 24, 2011—U.S. Appl. No. 11/622,654.

* cited by examiner

SYSTEM AND METHOD FOR MANIPULATING INSERTION PATHWAYS FOR ACCESSING TARGET SITES

CROSS-REFERENCE TO RELATED APPLICATIONS

This application is a continuation of U.S. patent application Ser. No. 11/622,654, filed Jan. 12, 2007, which claims the benefit of U.S. Provisional Patent Application Ser. No. 60/764,878, filed Feb. 3, 2006.

BACKGROUND OF THE INVENTION

1. Field of the Invention

This invention generally relates to a system and method for transferring a device from an initial insertion site on the body to a different insertion site on the body.

2. Description of the Related Art

The placement of a permanently or temporarily implantable device in the left side of the heart, and particularly the left atrium, may be difficult at a particular site of insertion because an operator must contend with the anatomical obstacles or equipment limitations presented by the catheter's route to the left heart. For example, it is more difficult to access the left atrium by performing an atrial transseptal puncture from an insertion point on the neck or near the shoulder than it is to perform a standard transfemoral Brockenbrough needle puncture of the intra-atrial septum from the right groin region. Because of the rigidity of the Brockenbrough catheter/needle system, the insertion site must provide a relatively straight path to the intra-atrial septum. A superior insertion site, however, provides a significantly tortuous and winding pathway to the intra-atrial septum, which makes the use of a Brockenbrough needle puncture technically more difficult from this insertion site. Still, there may be advantages to performing a medical procedure through a certain route that is difficult to catheterize. For example, it can be difficult to perform mitral balloon valvuloplasty from the inferior venous approach because an abrupt curve must be made in the left atrium to reach the mitral valve. When a valvuloplasty balloon is passed from a superior venous approach through the intra-atrial septum, there is a generally straight pathway to the mitral valve. Likewise, the implantation of certain medical devices may benefit from implantation through routes that are difficult to catheterize. One example is a medical device as described in U.S. Pat. No. 6,328,699, herein incorporated by reference, whereby a pressure transducer is placed on the left atrial side of the intra-atrial septum using transseptal catheterization. In some embodiments of the '699 patent, the pressure transducer is in continuity with a lead to a proximal housing that is more convenient when implanted in the subcutaneous tissue near the shoulder. Thus, although the catheterization is more readily performed from the groin region, the insertion of the implanted device from the shoulder is preferred.

SUMMARY

Several embodiments of the current invention provide a new method that allows transseptal catheterization of the left atrium from the standard transfemoral route via the groin that places the distal end of a guidewire in the vicinity of the left atrium followed by transfer of the proximal end from the groin to exit from a superior vein (subclavian or jugular).

In one embodiment, a method of transferring a guidewire from one insertion site to another insertion site is provided. In one embodiment, the method comprises the steps of introducing a first guidewire to a first insertion site, wherein the first guidewire has a proximal and distal end, introducing the distal end of the first guidewire to a target site, introducing a catheter having a proximal end and a distal end from a second insertion site and advancing the distal end of the catheter to the proximity of the first insertion site, introducing a second guidewire, wherein the second guidewire has a proximal and a distal end, through the catheter such that the distal end of the second guidewire extends out through the first insertion site, advancing the catheter over the second guidewire whereby a portion of the catheter emerges from the body through the first insertion site, and removing the second guidewire entirely from the catheter and inserting the proximal end of the first guidewire into the distal end of the catheter, whereby the proximal end of the first guidewire exist the proximal end of the catheter at the second insertion site. This method may further comprise snaring of distal end of the second guidewire with a snare and pulling the snare and the distal end of the second guidewire out from the first insertion site. In some embodiments of the invention, an introducer is placed at the first insertion site and/or second insertion site. In some embodiments, the introduction of the distal end of the first guidewire to a target site comprises introducing the distal end of the first guidewire to a site in the left atrium, right ventricle, pulmonary artery or renal artery. In some embodiments, the introduction of the catheter over the second guidewire from the second insertion site to the first insertion site comprises introducing a catheter from the second insertion site to a right femoral vein or right common carotid artery, or from a left femoral vein or left axillary vein to the first insertion site.

In one embodiment, another method of transferring a guidewire from one insertion site to another insertion site using a second guidewire is provided. In one embodiment, the method comprises the steps of introducing a first guidewire to a first insertion site, wherein the guidewire has a proximal end and a distal end, introducing the distal end of the first guidewire to a target site, introducing a catheter having a proximal end and a distal end from a second insertion site and advancing the distal end to the proximity of the first insertion site, introducing a second guidewire, wherein the second guidewire has a proximal end and a distal end, through the catheter such that the distal end of the second catheter extends out through the first insertion site, advancing the catheter over the second guidewire whereby a portion of the catheter emerges from the body through the first insertion site, engaging the proximal end of the first guidewire to the distal end of the second guidewire and withdrawing the catheter, second guidewire and the proximal end of the first guidewire from the second insertion site.

In one embodiment, another method of transferring a guidewire from one insertion site to another insertion site is provided, comprising the steps of introducing a guidewire through a first insertion site, introducing a catheter through a second insertion site to the first insertion site and inserting the proximal end of the guidewire into the distal end of the catheter whereby the proximal end of the guidewire exits the proximal end of the catheter at the second insertion site. In a further embodiment, the guidewire is introduced to a target site when the guidewire is introduced through the first insertion site. In another embodiment, when introducing the distal end of the catheter through a second insertion site to the first insertion site, the distal end of the catheter exits from the first insertion site.

In another embodiment of the invention, a method of transferring a guidewire from one insertion site to another insertion site using a conduit is provided. In one embodiment, the method comprises the steps of introducing the distal end of a guidewire through a first insertion site, establishing access to a second insertion site, introducing a conduit between the first insertion site and the second insertion site, where the conduit has a first end at the first insertion site and a second end at the second insertion site, inserting the proximal end of the guidewire into the first end of the conduit whereby the proximal end of the guidewire exists the second end of the conduit. In further embodiments of the invention, the conduit is a catheter. In still further embodiments, the step of introducing the conduit between the first insertion site and the second insertion site comprises introducing the catheter from the second insertion site to the first insertion site.

In another embodiment, another method of transferring a guidewire is provided, comprising the steps of providing a guidewire having a proximal end and a distal end, passing the proximal end and the distal end of the guidewire through a first insertion site in the body, where the distal end is passed before the proximal end, and externalizing the proximal end through a second insertion site of the body while the distal end remains in the body. This method may further comprise the step of passing a medical device over the guidewire into the body. The medical device may be a therapeutic or diagnostic medical device. The passing step may also involve a transseptal puncture. The externalizing step may involve inserting a snare through the second insertion site to engage the proximal end of the guidewire with the snare and withdrawing the snare and the proximal end of the guidewire from the second insertion site. One example of the first insertion site is the femoral vein, while one example of the second insertion site includes the subclavian vein.

In another embodiment of the invention, another method of transferring a guidewire from a first insertion site to another insertion site is provided. In one embodiment, the method comprises the steps of providing a guidewire with a proximal end, middle segment and a distal end, passing the proximal end and the distal end of the guidewire through a first insertion site into the body, wherein the distal end of the guidewire is passed before the proximal end of the guidewire and at least some portion of the middle segment remains external to the first insertion site, externalizing the proximal end of the guidewire through a second insertion site of the body while the distal end of the guidewire remains in the body and drawing the external portion of the middle segment into the body through the first insertion site. The method may further comprise the step of maintaining at least a portion of the middle segment of the guidewire outside the body while the proximal end and the distal end are inside the body.

In another embodiment, a method of transferring a guidewire from one insertion site to another is provided, comprising the steps of providing a guidewire having a proximal end and a distal end, inserting the distal end through a first insertion site of a body and through a pivot point in the body, inserting the proximal end through the first insertion site and externalizing the proximal end through a second insertion site without passing the proximal end through the pivot point.

In still another embodiment of the invention, a method of transferring a guidewire from one insertion site to another insertion site is provided. In one embodiment, the method comprises the steps of providing a guidewire having a proximal end and a distal end, passing the distal end the guidewire from a first insertion site in a body to a target site in the body, passing the proximal end of the guidewire from the first insertion site to a second insertion site, where the proximal end does not enter the target site when passing to the second insertion site. The method may further comprise the steps of providing a medical device and passing at least a portion the medical device along the guidewire from the second insertion site to the target site. The medical device may be a therapeutic or diagnostic medical device. One example of the first insertion site is a femoral vein, while one example of the second insertion site is a subclavian vein.

In one embodiment of the invention, a method of inserting a pacemaker lead through a sheath to the proximity of the left atrium is provided. In one embodiment, the method comprises the steps of providing a guidewire having a proximal end and a distal end, defining a first pathway from the right femoral vein to the left atrium through the right atrium, defining a second pathway from the right femoral vein to a subclavian vein through the right atrium; wherein the second pathway does not traverse the left atrium, defining a third pathway from the subclavian vein to the left atrium through the right atrium, passing the distal end of the guidewire along the first pathway, passing the proximal end of the guidewire along the second pathway, providing a sheath for passing a pacemaker lead, passing the sheath over the guidewire along the third pathway, withdrawing the guidewire from the sheath, providing a pacemaker lead and passing the pacemaker lead through the sheath along the third pathway, thereby inserting the pacemaker lead into the left atrium.

In other embodiments of the invention, a method of transferring a guidewire from one insertion site to another insertion site is provided. In one embodiment, the method comprises the steps of providing a guidewire having a proximal end and a distal end, defining a first pathway in a body from a first insertion site on a body to a target area in the body, defining a second pathway from the first insertion site to a second insertion site on the body, wherein the second pathway does not traverse the target area, defining a third pathway from the second insertion site to the target area, passing the distal end along the first pathway and passing the proximal end along the second pathway. The method may further comprise the steps of providing a medical device and passing at least a portion of the medical device along the third pathway. In further embodiments, the first pathway crosses the intraatrial septum. In other embodiments, the first, second and third pathways each pass through a junction area such as the right atrium. The medical device can be a therapeutic and/or diagnostic medical device. One example of the first insertion site is the femoral vein, while one example of the second insertion site includes the subclavian vein.

In another embodiment of the invention, a method of transferring a medical device component from one insertion site to another insertion site is provided. In one embodiment, the method comprises the steps of introducing a medical device component to a first insertion site, wherein the component has a proximal end and a distal end, introducing a guidewire to a second insertion site, wherein the guidewire has a proximal end and a distal end, introducing the distal end of the medical device component to a target site, introducing a catheter having a proximal end and a distal end over the second guidewire from the second insertion site to the first insertion site, wherein the distal end of the catheter exits the first insertion site, and inserting the proximal end of the medical device component into the distal end of the catheter whereby the proximal end of the medical device component exits the proximal end of the catheter at the second insertion site. Medical devices in this and other embodiments include, but are not limited to, clinical, diagnostic and therapeutic devices. Therapeutic devices include, but are not limited to, drug delivery devices, radiation agents, brachytherapy agents, pacemakers, defibrillators, valves, stents, sensors and pumps, and combinations thereof.

In another embodiment, a method of transferring a medical device component from one insertion site to another insertion site is provided. In one embodiment, the method comprises the steps of introducing the distal end of a medical device component through a first insertion site, wherein the component has a proximal end and a distal end, removably engaging the distal end of an extension device to the proximal end of the medical device component, wherein the extension device has a proximal end and a distal end, advancing the distal end of the medical device component to a target site, introducing a guidewire to a second insertion site, wherein the guidewire has a proximal end and a distal end, introducing a catheter having a proximal end and a distal end over the second guidewire from said second insertion site to said first insertion site, wherein the distal end of said catheter exits said first insertion site, inserting the proximal end of the extension device into the distal end of the catheter whereby the proximal end of the extension device exits the proximal end of the catheter at the second insertion site, and withdrawing the catheter and the extension device from the second insertion site whereby the proximal end of the medical device component is externalized through the second insertion site. In a further embodiment of the invention, in the step of advancing the medical device component to the target site, the proximal end of the extension device remains outside the body at the first insertion site when the medical device component is advanced entirely inside the body. The embodiment may also comprise the steps of snaring the distal end of the guidewire with a snare from the first insertion site and pulling the snare and the distal end of the second guidewire from the first insertion site. An introducer may also be placed at the first and/or the second introducer site. The target sites may comprise in the left atrium, right ventricle, pulmonary artery and coronary sinus. The first insertion sites may comprise the right femoral vein and right carotid artery. The second insertion sites may comprise the left femoral vein and the left axillary artery. The medical device component may comprise a second guidewire, an implantable sensor lead, or a temporary sensor lead.

Another embodiment of the invention provides a method of transferring a pacemaker lead from the right femoral vein to the right subclavian vein, comprising the steps of introducing the distal end of a pacemaker lead having a proximal end and a distal end through the right femoral vein, introducing the distal end of a catheter having a proximal end and a distal end through the right femoral vein and advancing the proximal end of the catheter to exit from the right subclavian vein, and inserting the proximal end of the pacemaker lead into the proximal end of the catheter whereby the proximal end of the pacemaker lead exits the distal end of the catheter at the right subclavian vein.

Another embodiment provides a method of transferring a medical device component from one insertion site to another insertion site, comprising the steps of introducing the distal end of a medical device component having a proximal end and a distal end through a first insertion site, introducing the distal end of a catheter having a proximal end and a distal end through the first insertion site and adjacent to a second insertion site, and inserting the proximal end of the medical device component into the proximal end of the catheter whereby the proximal end of the medical device component exits the distal end of the catheter at said second insertion site. The medical device component could be a pacemaker lead. One example of the first insertion site is the right femoral vein, while the second insertion site may be selected from the group consisting of one or more of the following, including the right subclavian vein, left subclavian vein, right jugular vein and left jugular vein.

In another embodiment of the invention, a method of transferring a medical device component from one insertion site to another insertion site is provided. In one embodiment, this method comprises the steps of providing a medical device component having a proximal end and a distal end, passing both the proximal end and the distal end of the medical device component through a first insertion site into a body, wherein the distal end is passed before the proximal end, externalizing the proximal end through a second insertion site of the body while the distal end remains in the body.

Another embodiment of the invention provides a method of transferring a medical device component from one insertion site to another insertion site. In one embodiment, this method comprises providing a medical device component having a proximal end and a distal end, passing both the proximal end and the distal end of the medical device component through a first insertion site into a body, wherein the distal end is passed before the proximal end, and externalizing the proximal end of the medical device component through a second insertion site of the body while the distal end remains in the body.

In another embodiment of the invention, a method of transferring a medical device component from one insertion site to another insertion site is provided. In one embodiment, this method comprises providing a medical device component having a proximal end and a distal end, passing the distal end of said medical device from a first insertion site of a body to a target site in the body; and passing the proximal end of the medical device through the body from the first insertion site to a second insertion site, wherein the proximal end does not enter the target site when passing to the second insertion site. Furthermore, the step of passing the proximal end of the medical device component of the comprises passing a snare from the second insertion site to the first insertion site, snaring the proximal end of the medical device component with the snare and withdrawing the snare and the medical device component from the second insertion site. One example of the medical device component is a pacing lead of a cardiac pacemaker. One example of the target site is the coronary sinus.

In another embodiment of the invention, a method of manipulating a device insertion pathway from one insertion site to another insertion site is provided. In one embodiment, this method comprises providing an insertion pathway between a first insertion site and a target site in the body, wherein the insertion pathway comprises a proximal segment, a distal segment and a pivot point between the proximal segment and the distal segment; and manipulating the proximal segment by pivoting the proximal segment at the pivot point from the first insertion site to a second insertion site, wherein the proximal segment does not overlap the distal segment.

In one embodiment of the invention, a kit for performing a transfer of a guidewire from one insertion site to another insertion site is provided. In one embodiment, the kit, system, collection, or combination of materials, comprises at least two guidewires and a catheter. The kit may also comprise a snare, at least one introducer and/or a Brockenbrough needle catheter. In some embodiments of the kit, at least one guidewire comprises a movable inner core mandrel.

In another embodiment of the invention, a guidewire for manipulating the insertion pathways to target sites in the body is provided. In one embodiment, this guidewire comprises a guidewire body with a proximal end, distal end and a middle segment, and an internal lumen comprising a movable core mandrel. The mandrel is operable to be inserted into the internal lumen during guidewire insertion and extracted from the internal lumen during guidewire transfer. The guidewire is at least about 180 cm in length. In further embodiments of the guidewire, the guidewire has a length of about 240 cm. In other embodiments of the guidewire, the internal lumen extends substantially through the length of the guidewire. In still other embodiments of the guidewire, the distal end of the guidewire is capable of a first configuration when the mandrel is in a retracted position and a second configuration when the mandrel is in an extended position. In some embodiments, the first configuration is a spiral coiled configuration or a J-shaped configuration. In some embodiments, the second configuration is a straight configuration or angled configuration.

In another embodiment of the invention, a guidewire with adjustable flexibility is provided. In one embodiment, this guidewire comprises a first component having a proximal end, a distal end and an elongate flexible body extending therebetween, and a second component, axially movably associated with the first component, the second component having a proximal end, a distal end and an elongate flexible body extending therebetween. The axial movement of one of the first and second components with respect to the other of the first and second components changes the lateral flexibility of the guidewire. At least one component of the guidewire has a length of at least about 180 cm. The first component may comprise a tube or a core. In some embodiments, the second component has an axial length within the range of about 20% to about 200% of the axial length of the first component. In other embodiments, the second component has an axial length of about 110% of the axial length of the first component. In still other embodiments, the guidewire is dimensioned to percutaneously enter and translumenally navigate a lumen for directing at least a component of a medical device to a remote target site.

In another embodiment of the invention, another guidewire with adjustable flexibility is provided. This guidewire comprises an elongate flexible tubular body having a proximal end and a distal end, a central lumen extending distally into the tubular body from the proximal end, and an elongate flexible core wire axially moveable within the central lumen. Axial proximal retraction of the core wire with respect to the tubular body increases the flexibility of at least a portion of the guidewire, and axial distal advance of the core wire with respect to the tubular body decreases the flexibility of at least a portion of the guidewire. The length of the elongate flexible tubular body is at least about 180 cm. In some embodiments of the invention, the portions of the guidewire capable of changes in flexibility define a flexibility zone of the guidewire. In some embodiments, the flexibility zone comprises at least about the proximal 90% length of the elongate tubular body. In other embodiments, the flexibility zone comprises generally the entire length of the elongate tubular body.

In another embodiment of the invention, another method of treating a patient is provided, comprising the steps of introducing a guidewire through a first access site into the patient's body, advancing the guidewire translumenally to a target site, adjusting the flexibility of the guidewire, and moving at least a portion of the guidewire to a second access site. In some embodiments, the step of adjusting the flexibility of the guidewire comprises distally advancing a core wire within the guidewire, while in other embodiments, it comprises distally advancing a tubular support around the outside of the guidewire.

In still another embodiment, a method of accessing a target site is provided. In one embodiment, this method comprises introducing a guidewire into a patient through an introduction site, the guidewire having a first, reduced flexibility, externalizing at least a portion of the guidewire through a different site of the body, and adjusting the guidewire to have a second flexibility. In further embodiments, the method also comprises the step of introducing a catheter along the guidewire after adjusting the guidewire to have a second flexibility.

Several embodiments of the invention provide these advantages, along with others that will be further understood and appreciated by reference to the written disclosure, figures, and claims included herein.

BRIEF DESCRIPTION OF THE DRAWINGS

The operation of the invention will be better understood with the following detailed description of embodiments of the invention, along with the accompanying illustrations, in which.

DETAILED DESCRIPTION

Several embodiments of the present invention generally relate to a system and method for performing catheterization of a body structure from a standard catheter insertion site, advancing a guidewire into the body structure from that insertion site, and transferring the proximal end of the guidewire to an alternative insertion site while leaving the distal end of the guidewire within the body structure. The transferred guidewire may then be used for the placement of a second device or to perform a desired procedure from the alternative insertion site. Some embodiments relate to methods for standard transseptal puncture of the left atrium from a femoral vein, where the guidewire is then transferred from the femoral insertion site to a subclavian vein insertion site for the implantation of a left atrial pressure-monitoring device. Several embodiments described herein are also generally applicable to other sites of catheter and device insertion. Methods for transferring a medical device or a medical device component, such as a pacemaker lead, between different insertion sites are also provided.

Figure 1:
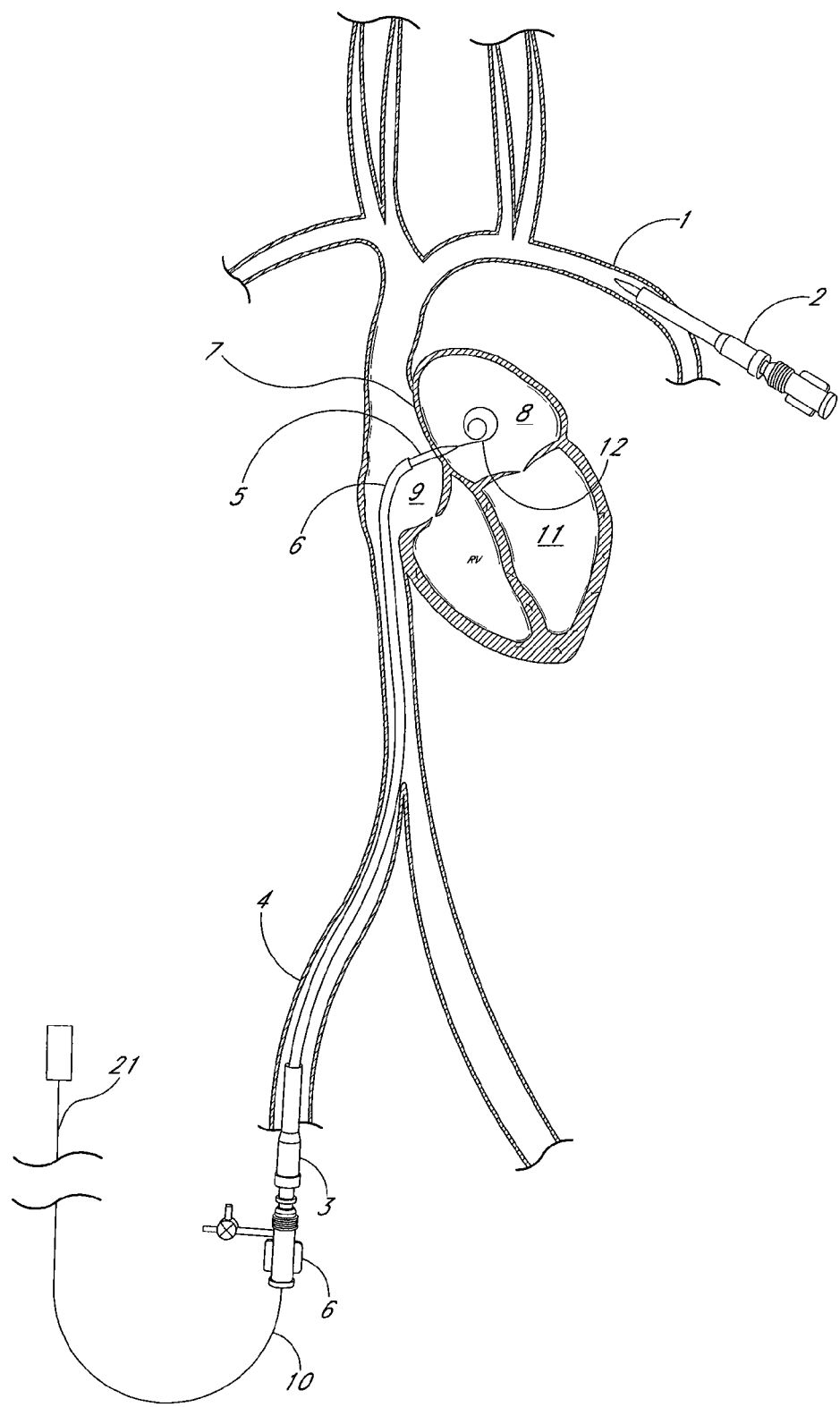
FIG. 1 shows a diagram of the central systemic veins and how they relate to the cardiac chambers. The left atrium has been catheterized by standard femoral transseptal technique and access to the left subclavian vein has been established using a standard large bore introducer sheath.

In one embodiment as shown in FIG. 1, the method involves gaining percutaneous or cut-down access into a superior central vein, such as the left subclavian vein 1 as shown, and may involve placing an introducer sheath 2 of appropriate caliber (typically 4-14 French) into the vein 1. A large bore introducer sheath 3 (typically 10-14 French) is then placed in the right femoral vein 4, generally by using either the Seldinger percutaneous method or via surgical cut-down technique, as described by Herbert Chen et al. in "Manual of Common Bedside Surgical Procedures", 29-76 (Herbert Chen et al. eds., 1996), herein incorporated by reference. From the right femoral access site, a standard transseptal cardiac catheterization is performed using a Brockenbrough needle (not shown), a catheter/dilator 5 and a 6 to 8-French Mullins sheath 6. This procedure entails the common practice that has been described many times in medical literature, as by Charles Davidson et al. in "Heart Disease: A Textbook of Cardiovascular Medicine", 369-370 (Eugene Braunwald et al. eds., 6th ed. 2001), herein incorporated by reference, involving a needle puncture of the septum 7 using fluoroscopic or ultrasonic visualization of the atrial septal anatomy. Once the puncture of the intra-atrial septum has been performed, the catheter/dilator 5 is advanced over the needle and into the left atrium 8. Ultimately, the Mullins sheath 6 can be advanced over the dilator into the left atrium 8, and the needle and dilator can be entirely removed from the sheath. If communication between the left atrium 8 and the right atrium 9 already exists, such as the presence of patent foramen ovale (PFO) or an atrial septal defect (ASD), access to the left atrium 8 can be performed without transseptal needle puncture and just by catheter and guidewire manipulation.

In one embodiment, after successful cannulation of the left atrium 8 from the femoral route, a guidewire 10 with a length between about 150 cm to about 300 cm can be placed in the left atrium 8 through the Mullins sheath 6. In another embodiment, the guidewire 10 has a length between about 180 cm to about 280 cm. In another embodiment, the guidewire 10 has a length between about 200 cm to about 260 cm. In yet another embodiment, the guidewire 10 has a preferred length of between about 220 cm to about 250 cm, preferably about 240 cm. The guidewire 10 may also have a length of less than about 150 cm or greater than about 300 cm. In one embodiment, the guidewire may comprise a moveable or removable core mandrel. Such guidewires include, but are not limited to, a stiffer type of movable core guidewire with a tapered tip on the distal core. In one embodiment, the guidewire distal portion 12 is soft and curled, and can be coiled in either the left atrium 8, left ventricle 11, left atrial appendage (not shown), or a pulmonary vein (not shown) to provide a stable distal position. One skilled in the art will understand that many types of such coils can be used to achieve a stable anchoring position for the distal end of the guidewire. In one embodiment, the core can be at least partially pulled back to increase the coiling propensity of the wire. The Mullins sheath 6 or catheter is then withdrawn while maintaining the distal guidewire 12 position.

Figure 2:
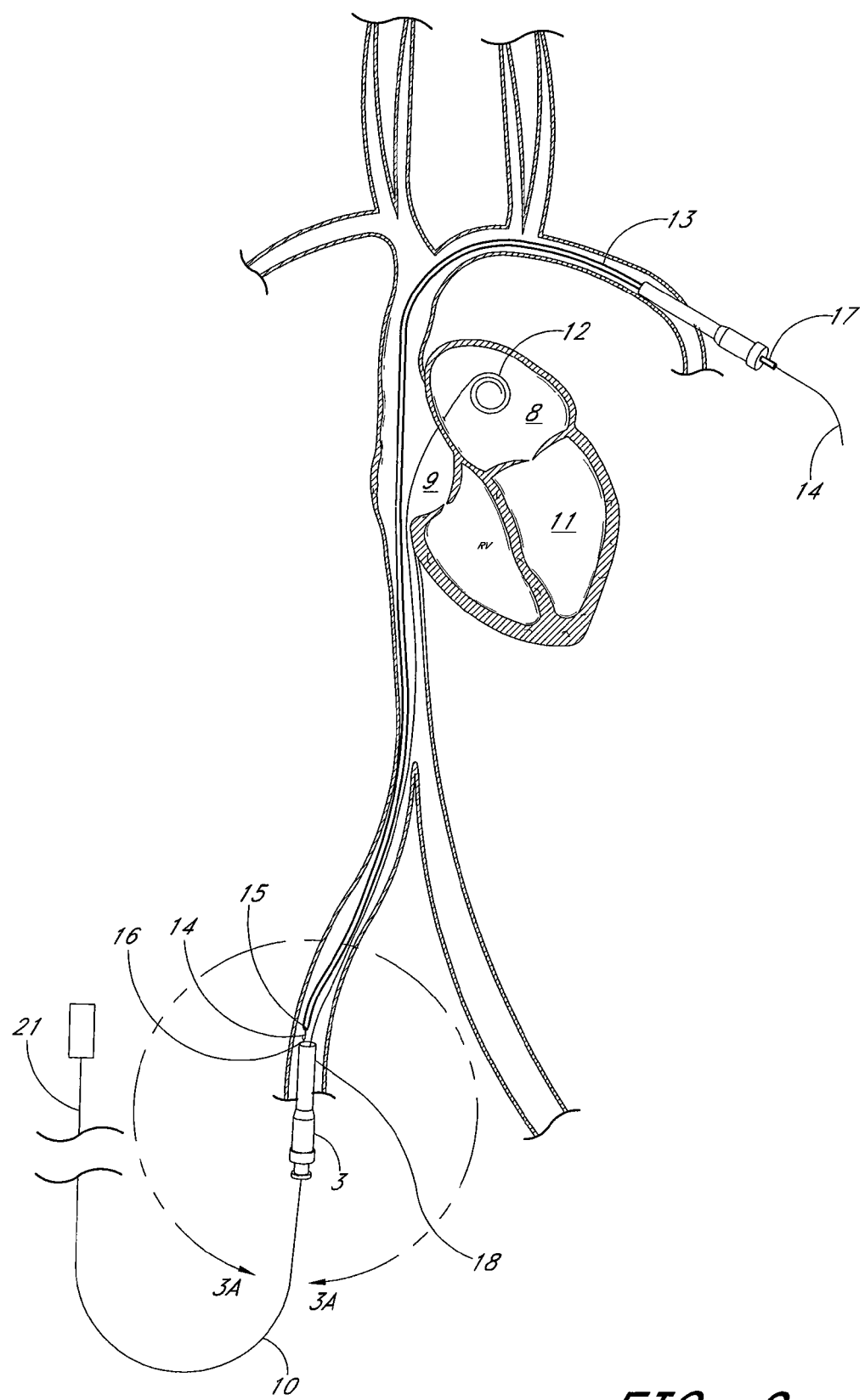
FIG. 2 shows one step in one embodiment of placing a catheter from a subclavian vein entry site and having the catheter exit through the same femoral vein access site that was used for the transseptal catheterization.
Figure 3A:
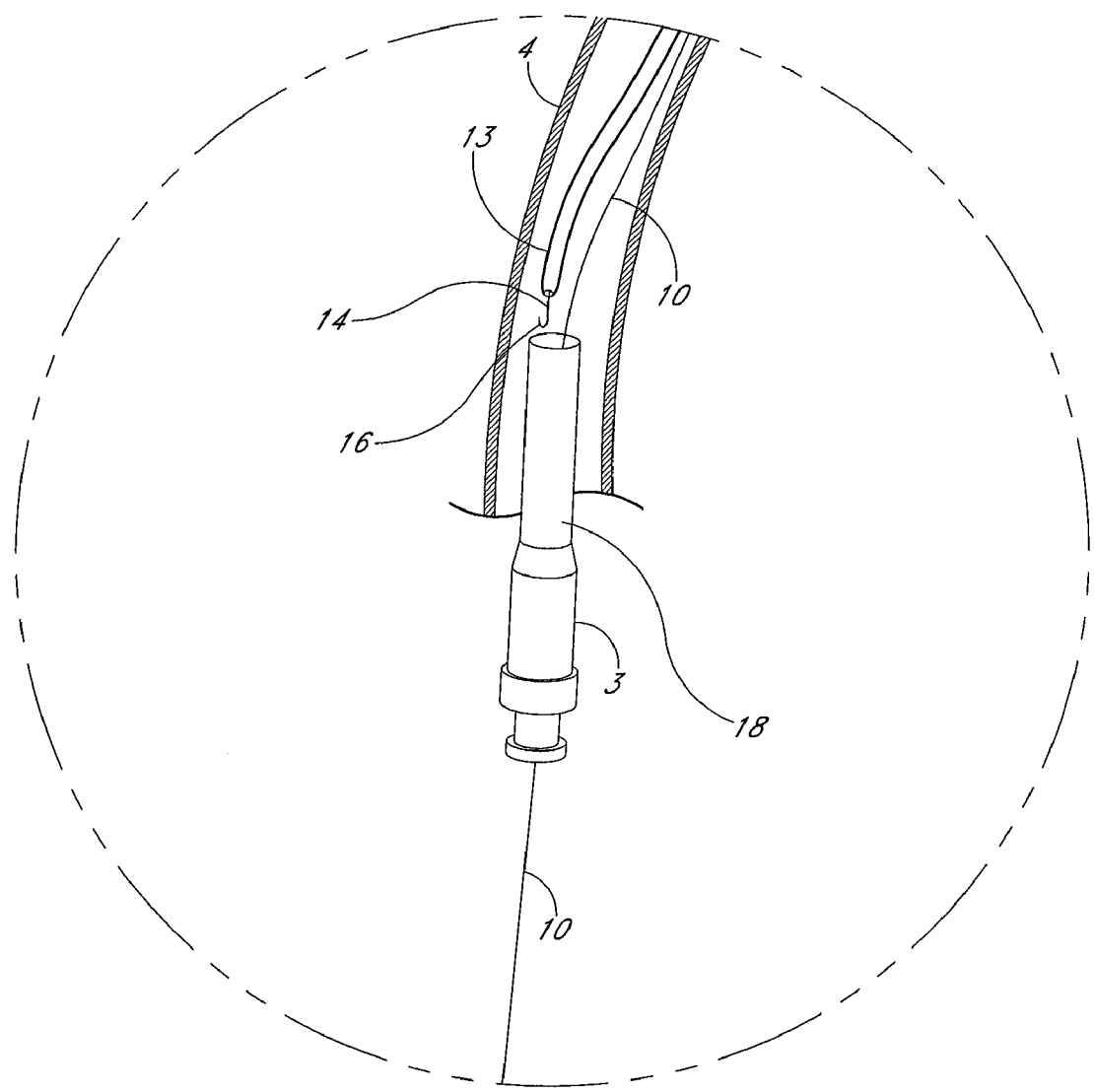
FIGS. 3A through 3D detail further steps in one embodiment according to the present invention for passing a catheter from a subclavian vein entry site to a femoral vein access site, preparatory to transferring the proximal end of a guidewire from the right femoral vein to a desired access site in the left subclavian vein.

As shown in FIG. 2, in one embodiment, a torqueable catheter 13 is inserted through the subclavian vein sheath 2 over a standard guidewire 14 (diameter typically 0.025-0.038 inches). In one embodiment, the catheter 13 has a diameter of about 4 French to about 6 French and length of about 80 cm to about 100 cm. In one embodiment the catheter 13 has a tip 15 configured with a bend near the distal end, such as a "multipurpose", "Judkin's right" or "Cobra" shape catheter that allows the tip to be steered by rotating the catheter. Skilled artisans will understand that catheters with a variety of distal tip shapes may be used to enhance steerability through branching or tortuous anatomy. Referring now to a close-up of the femoral access area shown in FIG. 3A, the wire tip 16 may be straight, or it may have a small "J", angled or a bendable distal tip that can be used for steering. One skilled in the art will understand that several shapes and curvatures for the wire tip may be used in accordance with several embodiments of the present invention. The wire 14 and catheter 13 are advanced and manipulated by applying a torque force to the proximal shaft 17 of the catheter 13, wire 14, or both, until they engage the distal end 18 of the femoral vein sheath 3. Care should be taken to minimize entangling the catheter 13 around the previously placed guidewire 10 extending from the left atrial site 8 through the femoral sheath 3.

Figure 3B:
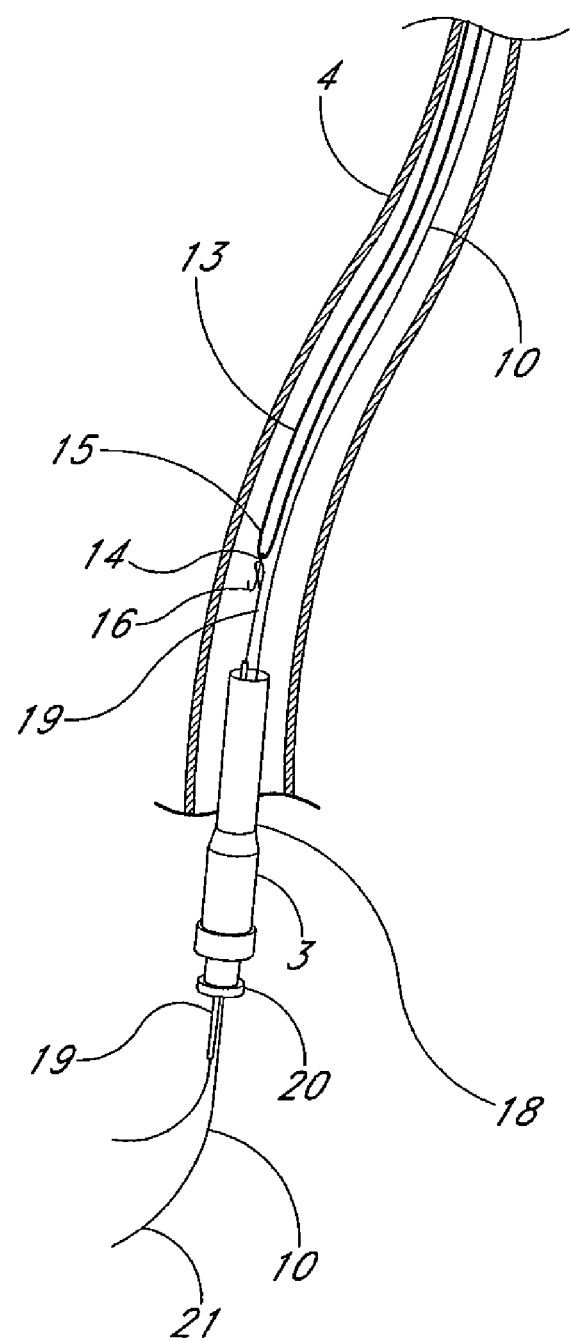
Figure 3C:
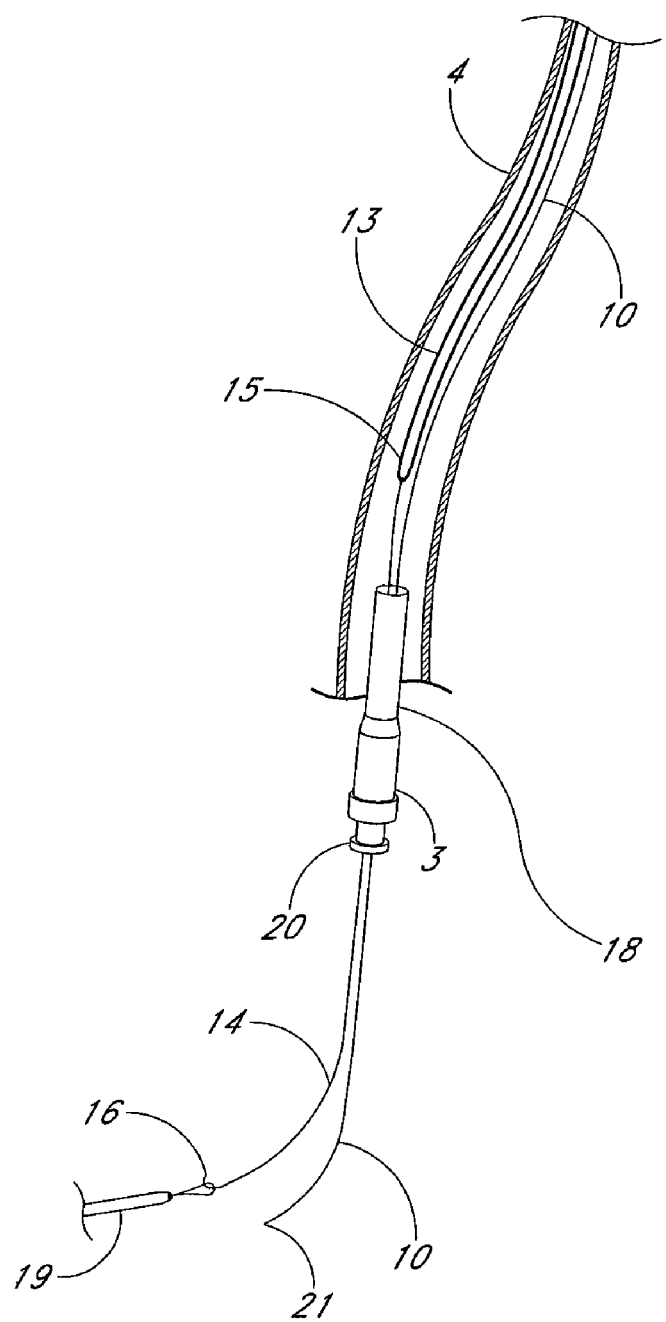
Figure 3D:
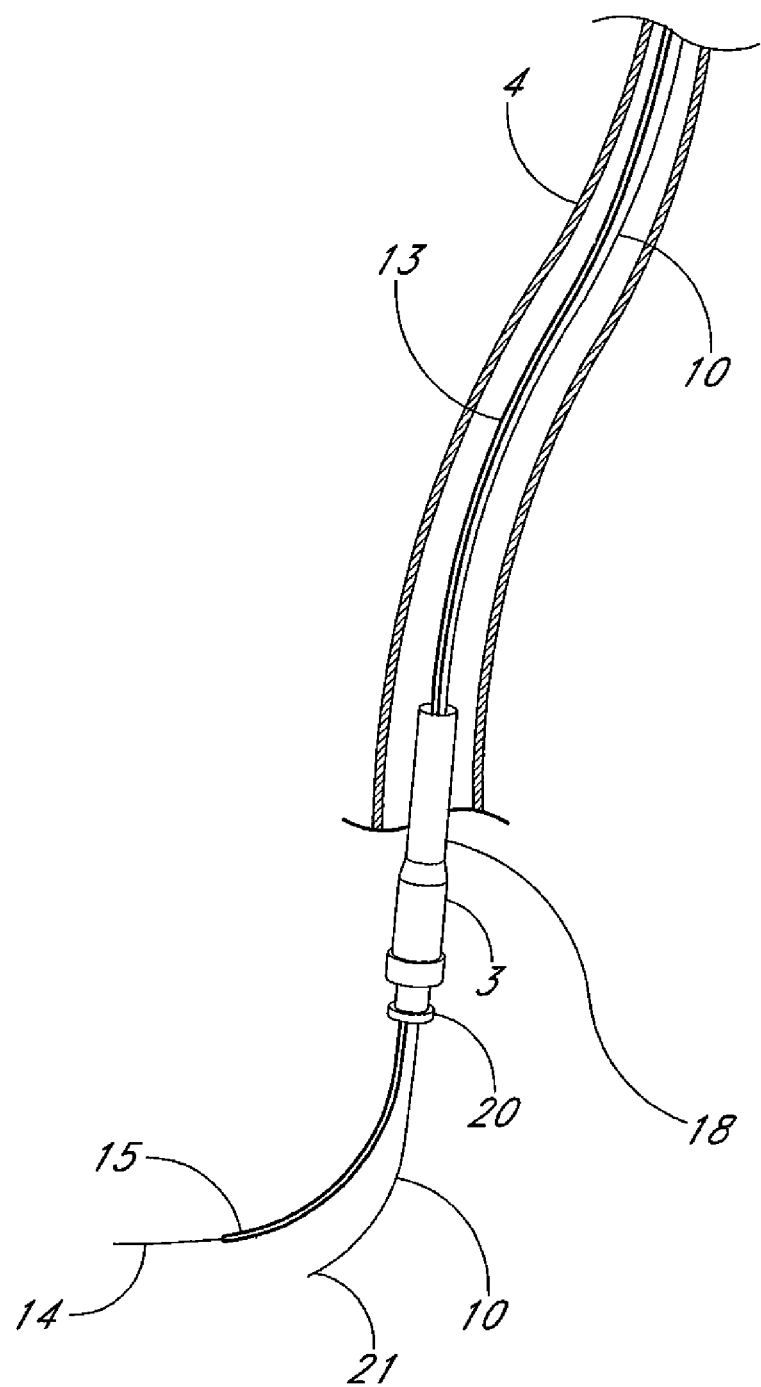

As shown in FIG. 3B, if difficulty is encountered entering the distal sheath 18 of the femoral vein 4 with the tip 16 of the superiorly placed guidewire 14, the guidewire tip 16 can be grabbed with a commonly available "goose neck" snare 19 (e.g., such as snares available from Microvena Corp., MN) inserted into the femoral sheath 3 and then pulled through the sheath 3 until the distal tip 16 of the guidewire 14 exits through a hemostasis valve 20 of the femoral sheath 3 at the patient's groin, as depicted in FIG. 3C. It may also be helpful to use a thin walled introducer (not shown) placed over the inferiorly inserted guidewire through the hemostasis valve 20 to facilitate the passage of the superiorly placed guidewire 14 and catheter 13 through the hemostasis valve 20. In one embodiment, once the distal tip 15 of the superior catheter 13 exits the femoral vein sheath 3, as depicted in FIG. 3D, the superiorly placed guidewire 14 is removed from the superior catheter.

Figure 4:
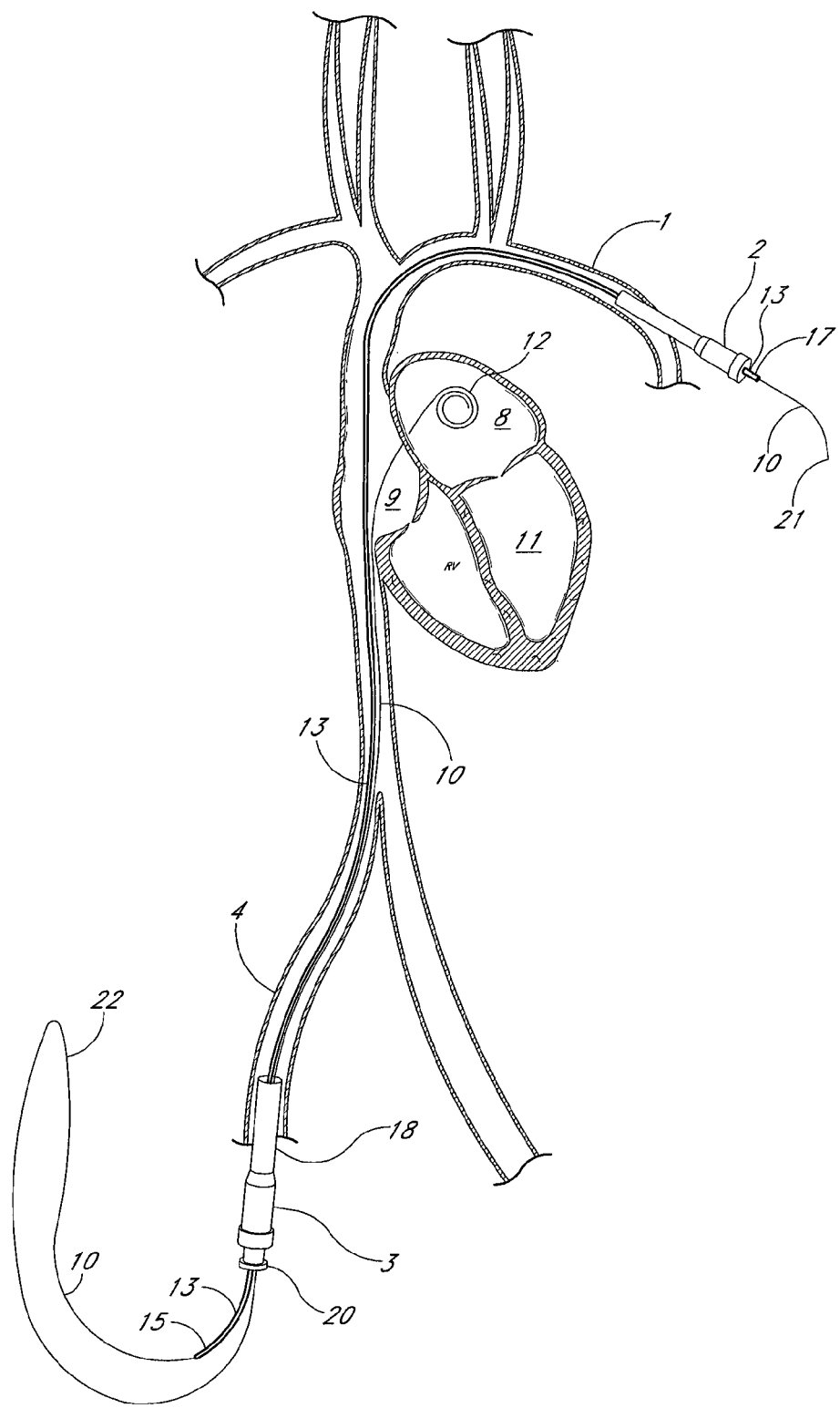
FIGS. 4 through 7 show the steps in one procedure according to the present invention in which a guidewire used for the left atrial catheterization is transferred from the femoral access site to the subclavian access site.

In one embodiment, as shown in FIG. 4, the inferiorly placed guidewire 10, whose distal portion 12 is located in the left atrium 8, is configured so that the proximal end 21 of this guidewire 10, after removing its movable core, is now inserted into the distal tip 15 of the superior catheter 13 exiting the femoral sheath 3. In one embodiment, removal of the movable core advantageously increases the flexibility of the wire body so it will not be plastically deformed (kinked) during subsequent manipulations. In another embodiment, a small kink may be tolerated. In yet another embodiment, a single-piece guidewire constructed from superelastic nitinol or other material with similar properties as known in the art may be used to provide a guidewire that is more kink-resistant than traditional stainless steel guidewires and does not require a moveable core mandrel. One skilled in the art will understand that many such guidewire configurations exist and may be applicable. The proximal end 21 of this guidewire 10 is passed until its proximal end 21 exits from the proximal end 17 of the subclavian catheter 13. Thus, the proximal end 21 of the transseptal wire is "backloaded" into the distal tip 15 of the catheter 13 exiting the femoral vein sheath 3 and is advanced until it protrudes from the proximal shaft 17 of the catheter 13. In another embodiment, the catheter tip 15 is advanced to the inferior insertion site in the right femoral vein 4 but it does not exit the inferior introducer sheath 3. The guidewire 10 may be backloaded into the distal tip 15 of the catheter 13 under fluoroscopic or ultrasonic guidance, or by using a snare 19 inserted through the catheter 13 from its superior proximal end 2. In yet another embodiment, the proximal end 21 of the inferior guidewire is docked into the distal end of the superior guidewire 14 such that the two wires 10, 14 form a single continuous loop from the superior subclavian entry site, out through the femoral sheath 3, back through the femoral sheath, and ending in the target site 8. The skilled artisan, such as an interventional cardiologist or radiologist, will be familiar with several types of docking mechanisms that have been developed for attaching two guidewires together.

Figure 5:
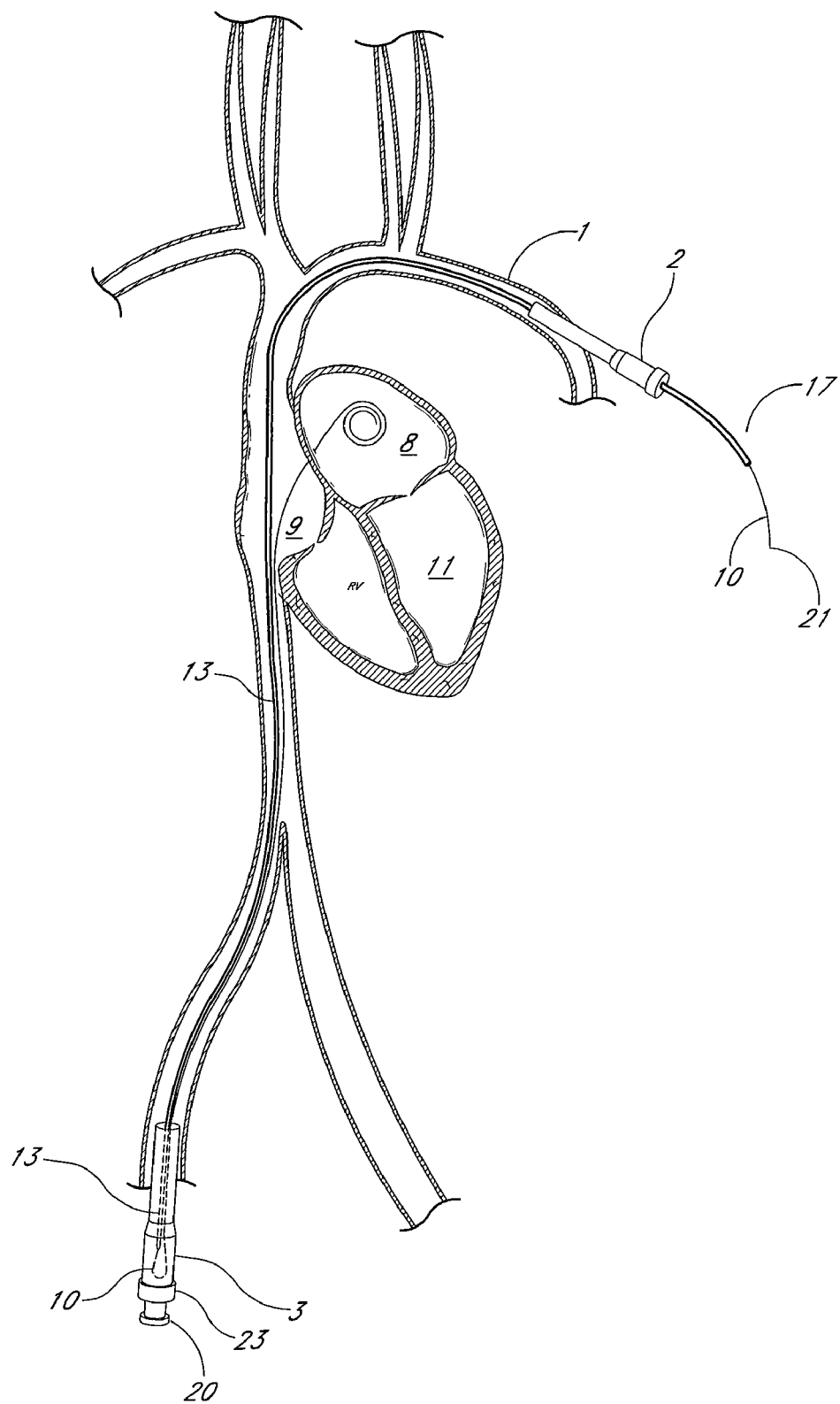

In one embodiment, advancement is continued until a small loop 22 is left exiting the femoral sheath 3, as depicted in FIG. 4. Referring to FIG. 5, the catheter 13 and guidewire 10 are withdrawn from the superior insertion site in the left subclavian vein 1. In one embodiment, the catheter and guidewire are withdrawn as a unit. In another embodiment, the catheter and guidewire may be manipulated individually during withdrawal to alter their relative positions as indicated to the operator by visual, auditory, mechanical, or other means, such as by fluoroscopy or ultrasonography. A thin-walled introducer (not shown) may be advanced over this loop into the hemostatic valve 20 of sheath 3 to facilitate pulling the loop 22 through the valve 20 and into the catheter 13. In one embodiment, the movable core is withdrawn into the catheter 13 so that the wire exiting the catheter 13 and sheath 3 in the groin contains no core and has increased flexibility during the transfer maneuver just described.

Figure 6:
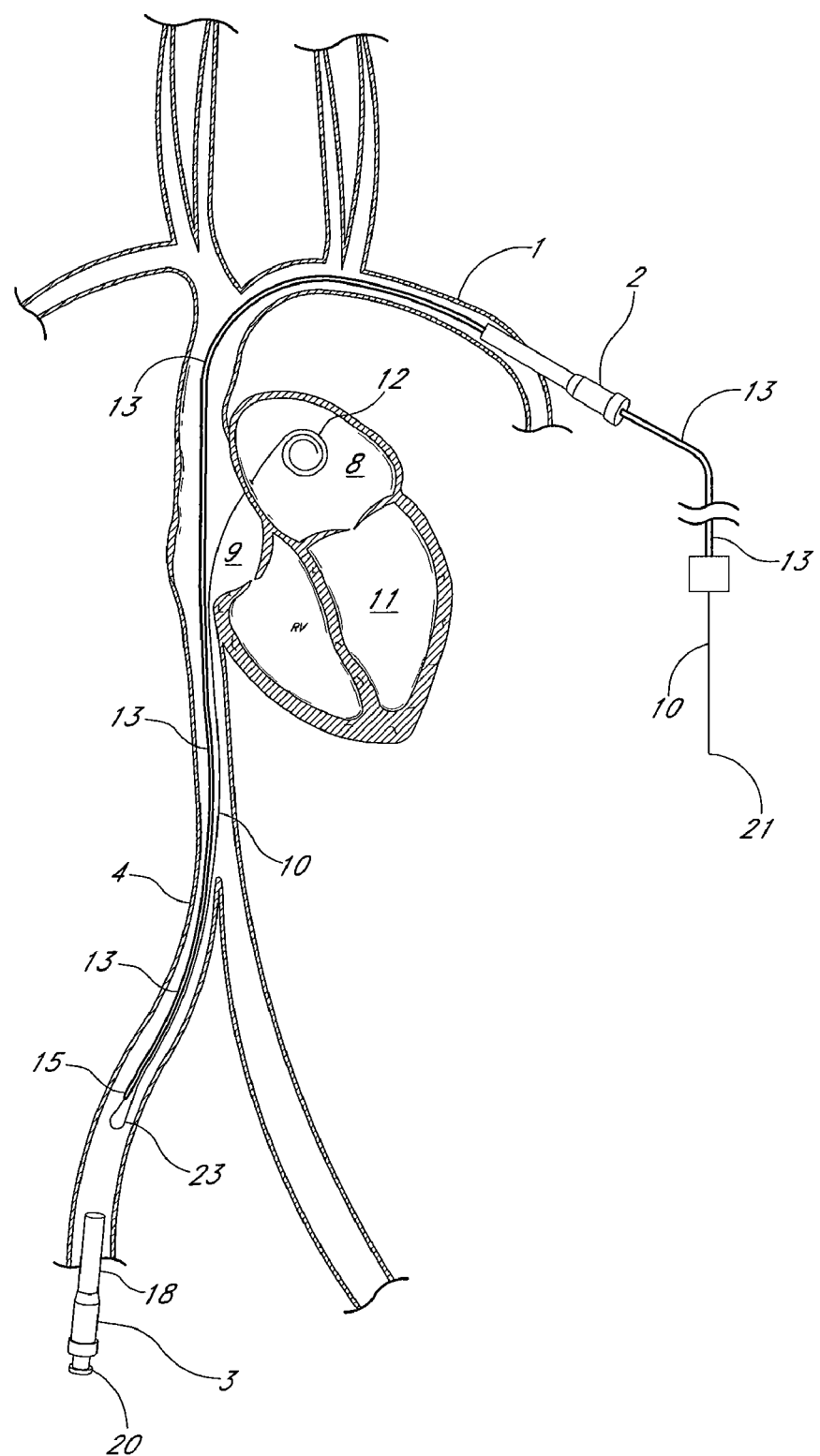

In one embodiment, the guidewire 10 is sufficiently flexible without the core such that it is capable of creating at least a tight 180 degree bend 23 in the venous system without injuring the wire or the venous system, as illustrated in FIG. 6. In another embodiment, the guidewire 10 is capable of bending at least about 180 degrees in a lumen between about 0.5 cm to about 4 cm, preferably between about 0.75 cm to about 1.5 cm, and more preferably about 1 cm.

Figure 7:
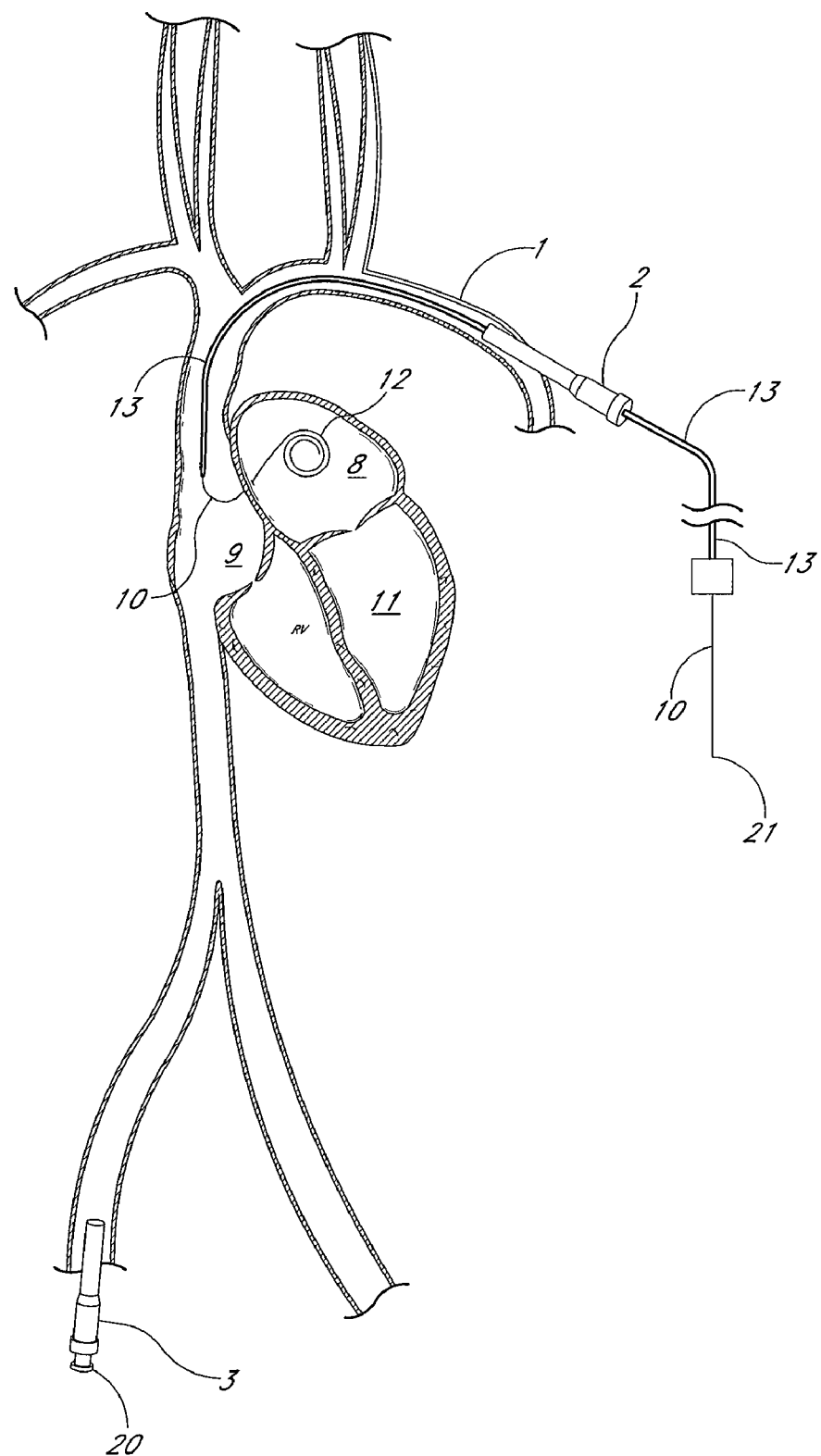
Figure 8:
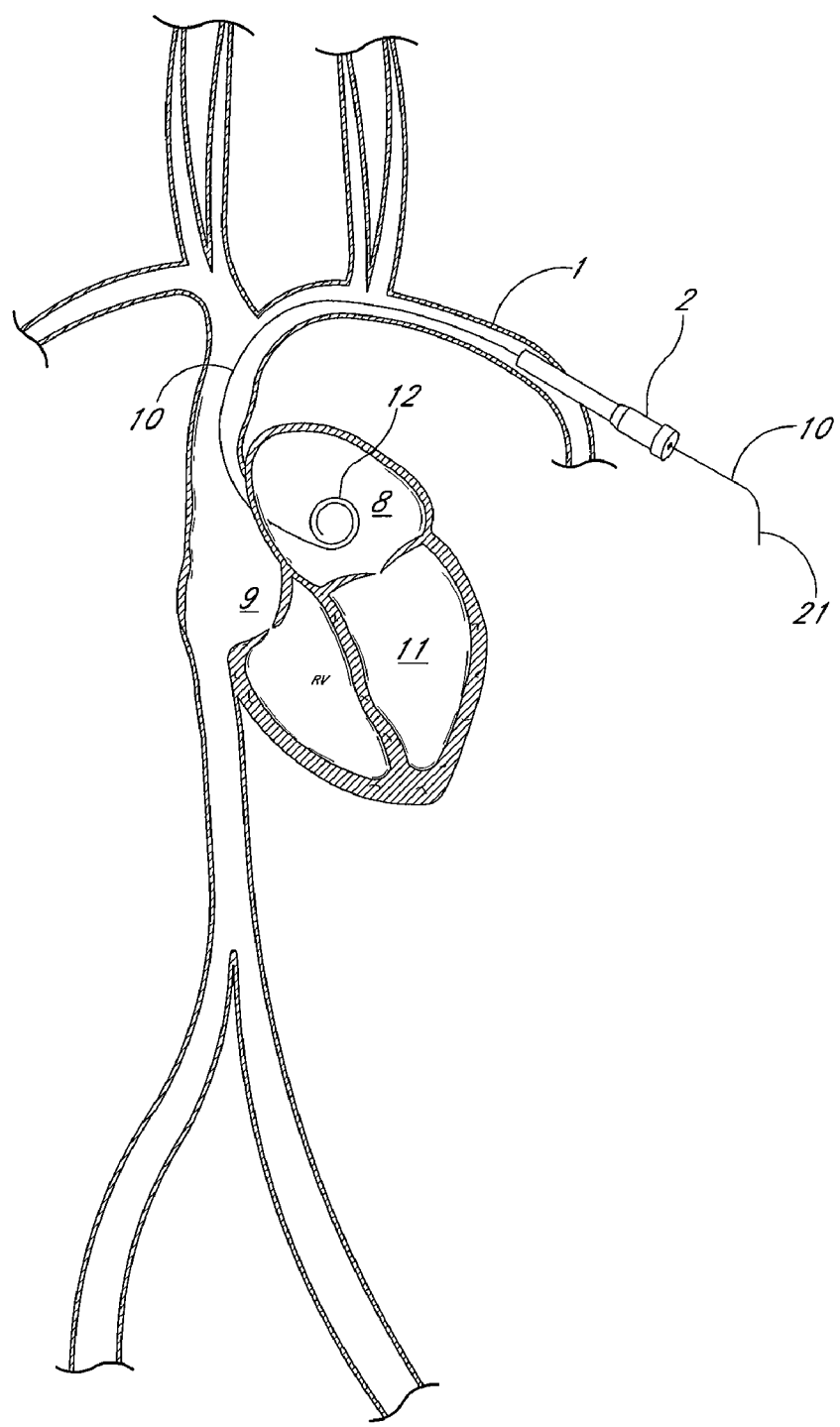
FIG. 8 demonstrates how the guidewire, once transferred, can be stiffened to allow over-the-wire insertion of other devices from the subclavian site

As shown in FIG. 7, in one embodiment, as the catheter 13 is removed, the distal position of the guidewire 10 is maintained in the left atrium 8. Once the catheter 13 is removed, only the guidewire 10 exits the sheath 2 in the subclavian vein 1. The wire 10 may have a minimal kink where it had previously formed a tight loop 23, but this area of the kink is external to the patient, having exited the subclavian sheath 1. The movable inner core mandrel is re-advanced such that it crosses the intra-atrial septum 7 and is in the left atrium 8 to help facilitate catheter transfer over this stiffened guidewire 10, as shown in FIG. 8.

Figure 9:
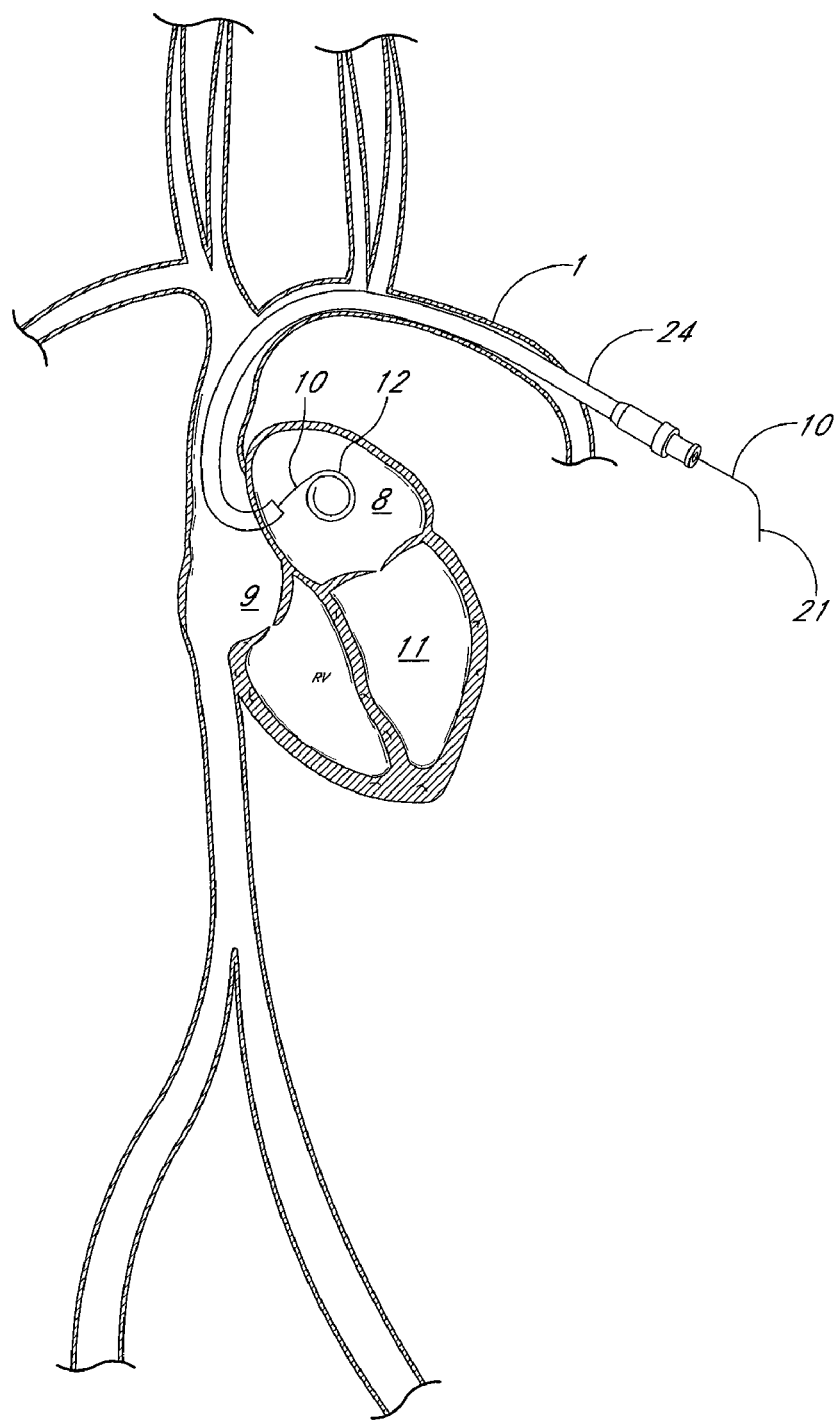
FIG. 9 shows the insertion of a large bore sheath over the transferred wire, through the atrial septum, and into the left atrial site from the subclavian access route.
Figure 10:
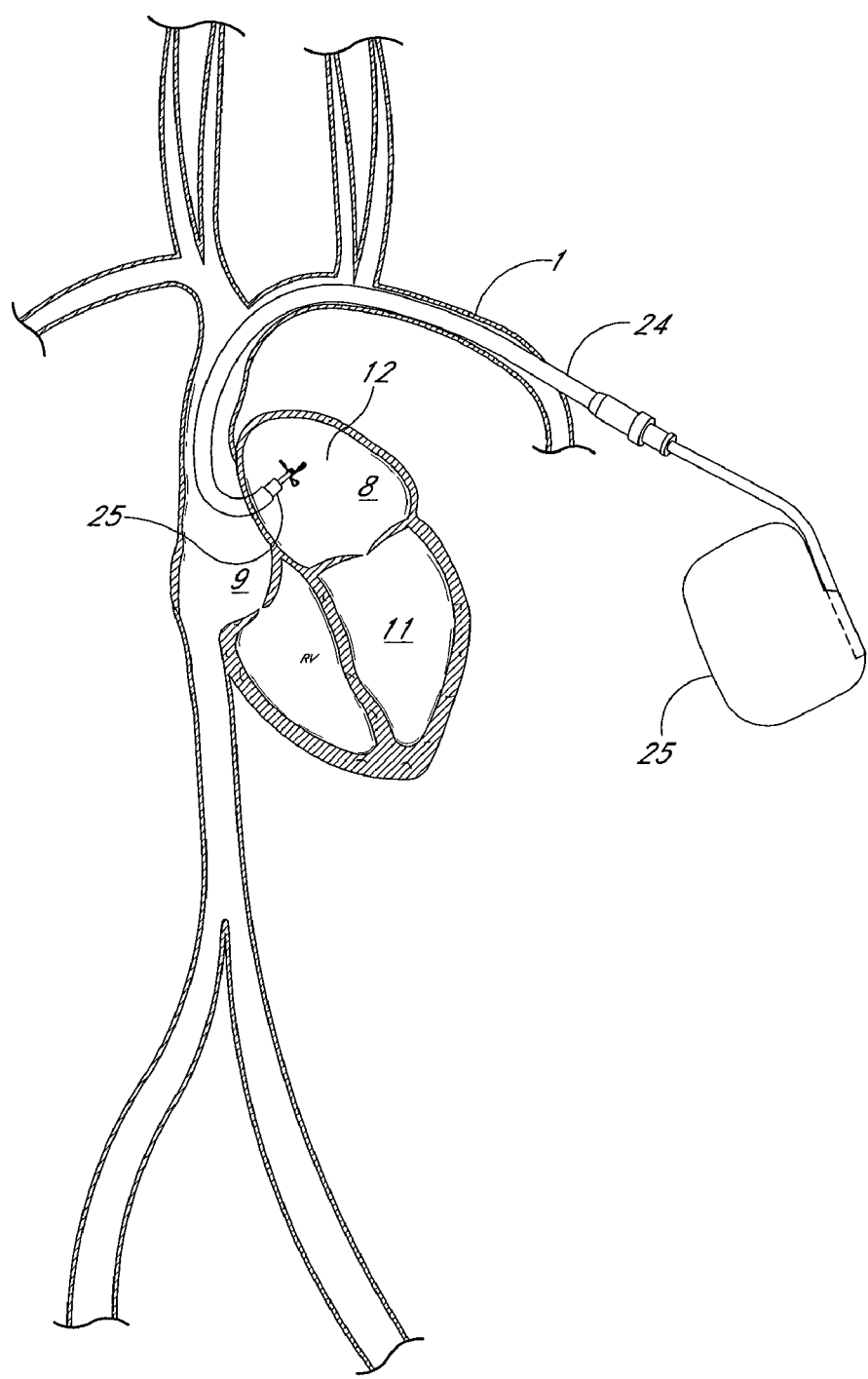
FIG. 10 demonstrates the placement of an implantable device on the intra-atrial septum from a superior venous approach.

Referring now to FIG. 9, the subclavian sheath 2 can be replaced by a large bore introducer 24, which is advanced over the guidewire 10 and placed in the left atrium 8. In one embodiment, the large bore introducer 24 is of the "peel away" type, commonly used by skilled artisans for placement of implantable medical devices with a larger proximal diameter such as an implantable pacing or defibrillator lead that is connectable to a proximal housing 25, such as a pacemaker or defibrillator generator. In one embodiment, the introducer 24 may facilitate placement of one or more medical devices 25 and/or devices for closure of the left atrial appendage. Medical devices include, but are not limited to, a pacemaker lead, a patent foramen ovale closure device, and a device for measuring left atrial pressure 26, shown in FIG. 10. In another embodiment, the guidewire, if positioned into the left ventricle, may be used to advance a mitral valvuloplasty balloon. One skilled in the art will understand that several diagnostic and therapeutic applications can be used in accordance with several embodiments of the present invention.

In a further embodiment of the invention, the inferior guidewire 10 is not positioned in any particular target site when the guidewire transfer is performed, but is advanced to the target site after the guidewire transfer is performed. In another embodiment, the distal position of the guidewire 10 is not maintained in any particular position or body structure but a middle portion of the guidewire 10 passes through and is constrained by a body structure, such as the intra-atrial septum. This body structure may act as a pivot point to allow movement of the guidewire portion between the pivot point and the proximal end of the guidewire 10 while constraining at least a portion of the movement of the guidewire 10 at the body structure.

Several embodiments of the present invention are particularly advantageous because of their applicability to the general case of transferring a wire from one insertion site in the venous or arterial circulation to another exit site for that wire in the same circulation. Other, insertion sites that may be used with several embodiments of the invention include, but are not limited to, the radial arteries, dorsalis pedis arteries, axillary arteries and internal jugular veins. Access to these sites are known to those in the art and are described by Herbert Chen et al. in "Manual of Common Bedside Surgical Procedures", 29-76 (Herbert Chen et al. eds., 1996), herein incorporated by reference. Several embodiments of the invention also provide for other target sites, including the right ventricle, left ventricle, pulmonary arteries, pulmonary veins, renal arteries, renal veins, portal veins, hepatic arteries, carotid arteries, jugular veins, axillary arteries, axillary veins and pathological sites such as an abdominal aortic aneurysm.

Several embodiments of the invention are also advantageous because of their general applicability to the concept of transferring the proximal end of a guidewire from a first insertion site to a second insertion site, after inserting the distal end of the guidewire from the first insertion site toward a target site or in proximity of a target site. In one embodiment, the insertion and transfer of a guidewire defines a series of pathways in the body taken by the proximal and distal ends of the guidewire. The initial insertion of the distal end of the guidewire is capable of defining a first pathway between the first insertion site and a target site. The transfer of the proximal end of the guidewire from the first insertion site and the second insertion site is capable of defining a second pathway taken by the proximal end of the guidewire. By transferring the proximal end of the guidewire, a third pathway is then defined along the new guidewire position, from the second insertion site to the target site. The third pathway may be used to access the target site.

In some embodiments of the invention, a conduit is placed between the first insertion site and second insertion site to facilitate transfer of the proximal end of the guidewire. In the preferred embodiment, the conduit comprises a catheter inserted from the second insertion site to first insertion site, but one skilled in the art will understand that the conduit may comprise any structure that provides a lumen generally between the first insertion site and the second insertion site and that the conduit may be inserted between the insertion sites in other ways. For example, the conduit may be placed from the first insertion site to the second insertion site. In other embodiments, a conduit is not used to transfer the proximal end of the guidewire and the guidewire is transferred by other devices, such as a snare that pulls the proximal end of the guidewire from the first insertion site to the second insertion site.

In some embodiments of the invention, portions of the first pathway and the third pathway may overlap. For example, in one embodiment of the invention, the first insertion site is the right femoral vein, the second insertion site is the right subclavian vein and the target site is the left atrium. The first pathway from the right femoral vein to the left atrium, and the third pathway, from the right subclavian vein to the left atrium, share a common distal portion from the intra-atrial septum to the left atrium. The most proximal point common to both the first and third pathways define a pivot point whereby the distal portions of the first and third pathways are constrained to at least partially overlap and where the portions proximal to the pivot point do not overlap. In one embodiment, the second pathway taken by the proximal end of the guidewire does not cross or intersect the pivot point or the target site, but may pass through structures that the first and third pathways also pass through. Such structures are defined as junction areas and typically, but not always are situated proximal to the pivot point and/or target area. In the example mentioned above, all three pathways will pass through a junction comprising the right atrium.

In another embodiment, a patient is treated by introducing a guidewire into a patient at a first access site and advancing the guidewire translumenally to a target site. The flexibility of at least a portion the guidewire is adjusted and is transferred to a second access site. In one embodiment, the adjustment of the guidewire flexibility is performed by moving a core wire within the guidewire. In another embodiment, the flexibility is adjusted by advancing a tubular support around the outside of the guidewire.

In another embodiment of the invention, a method for accessing a target site is provided, where a guidewire is introduced into a patient through an introduction site, the guidewire having a first, reduced flexibility. The guidewire is then adjusted to a second flexibility to advantageously externalize at least a portion of the guidewire through a different introduction site of the body. A catheter is then introduced along the guidewire.

In one embodiment, this procedure may be used to cannulate the coronary sinus in the right atrium from the usual superior venous approach. Using the methodology of one embodiment of the present invention, once a guidewire is placed in the coronary sinus, a catheter can be threaded from an inferior venous approach to exit from the superior introducer site. A withdrawal of the guidewire core creates a soft bend, followed by backloading of the wire into the distal end of the catheter until it exits the proximal end of the catheter shaft in the groin. The catheter is subsequently withdrawn and accomplishes transfer of the wire from a superior insertion site to an inferior insertion site. This approach could be used for placing the left ventricular lead of a cardiac resynchronization pacemaker (biventricular pacemaker) when the rhythm management system generator must be placed in the lower abdominal wall. Similar approaches can be performed on the arterial side of the circulation as well. In accordance with many embodiments of the current invention, similar approaches can be performed when cannulating any orifice in any hollow viscus in the body of an organism, including but not limited to the gastrointestinal system, urinary system, reproductive system and central nervous system. For example, in some embodiments of the invention, the oropharynx, nasopharynx, rectum, urethra may be used as insertion sites. In other embodiments of the invention, artificial locations, such as a ventriculoperitoneal shunt, nephrostomy tube or gastric tube, may be used as insertion sites.

Figure 11A:
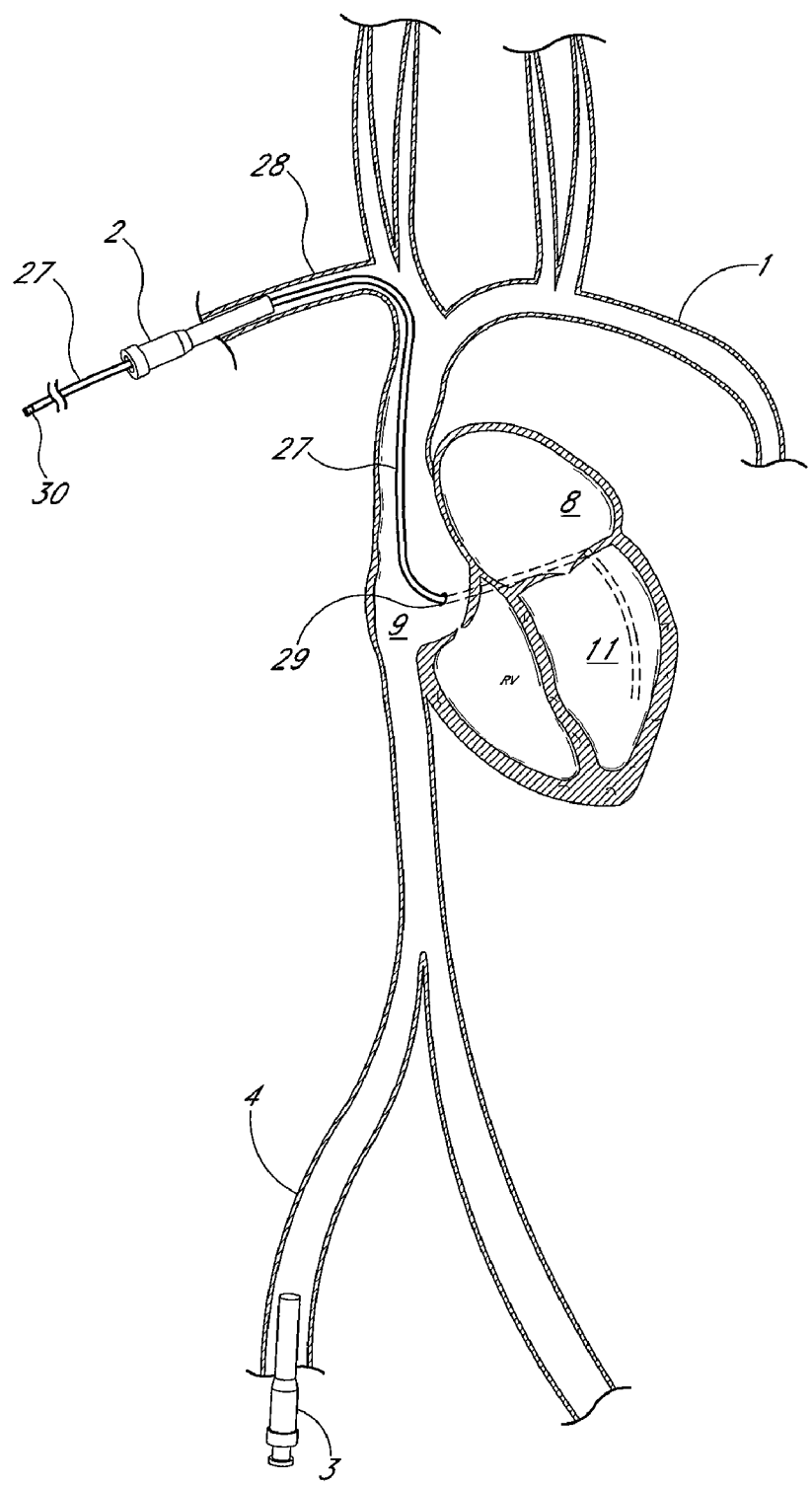
FIGS. 11A through 11D show the insertion of a pacing lead at the right subclavian vein and transfer of the lead to the right femoral vein.

In addition to embodiments of the invention for transferring guidewires, several embodiments of the invention may be adapted to provide for the transfer of at least a portion of a device from one insertion site to another insertion site, with or without the device on a guidewire. Devices capable of such transfer include but are not limited to sensor leads, pacing leads, catheters and any other medical device or portion of a medical device that is capable of movement through a body lumen of an organism. For example, FIG. 11A depicts the insertion of a left ventricular lead 27 of a biventricular pacemaker described previously. In one embodiment, the lead 27 is inserted through a first insertion site at the right subclavian vein 28 and into the coronary sinus 29 in the right atrium 9. A catheter is inserted into a second insertion site at the right femoral vein, through the inferior vena cava, right atrium and superior vena cava and externalized through the first insertion site. The lead is backloaded into the catheter and exits from the second insertion site. The catheter and lead are withdrawn from the second insertion site.

Figure 11B:
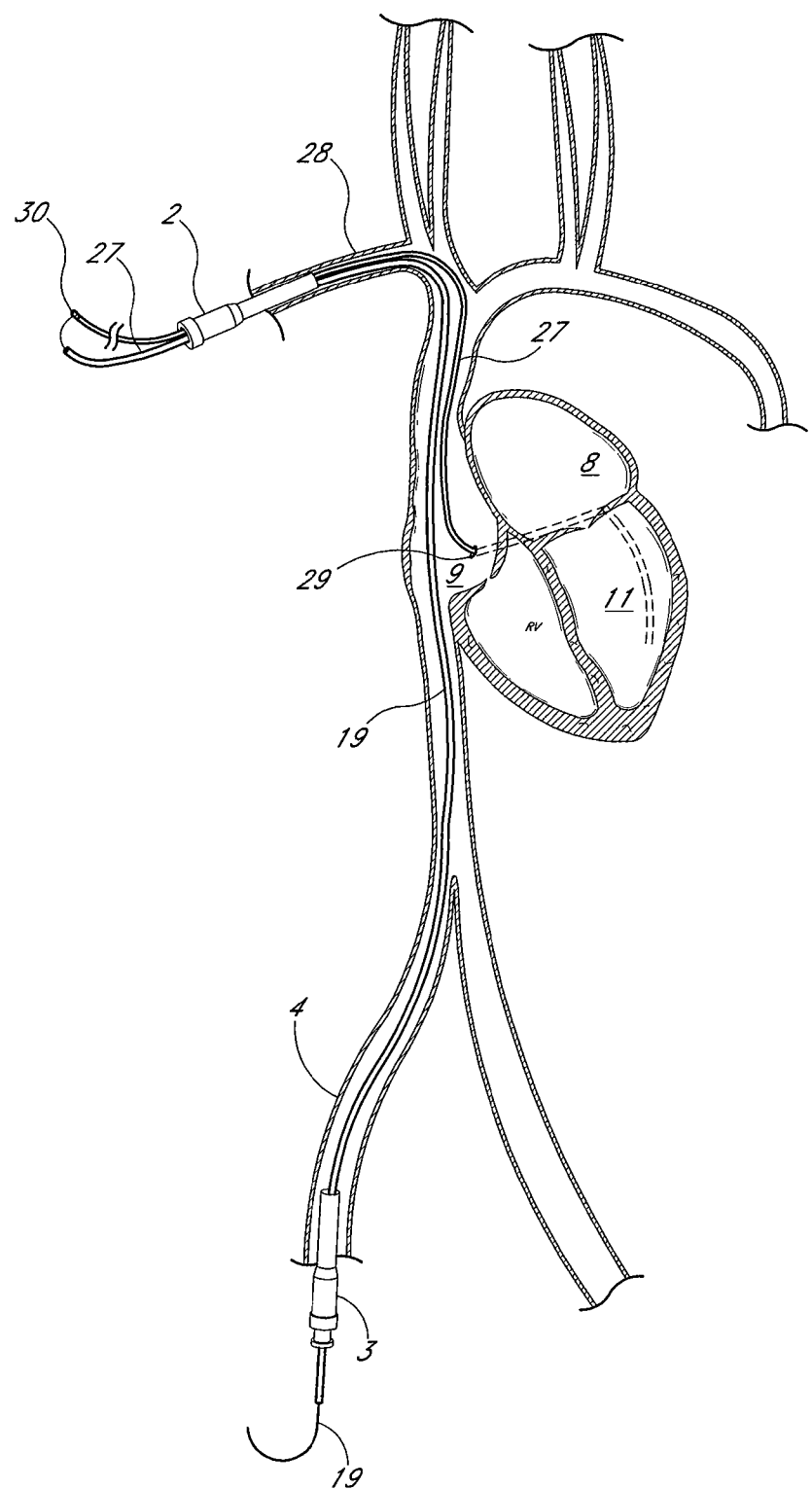
Figure 11C:
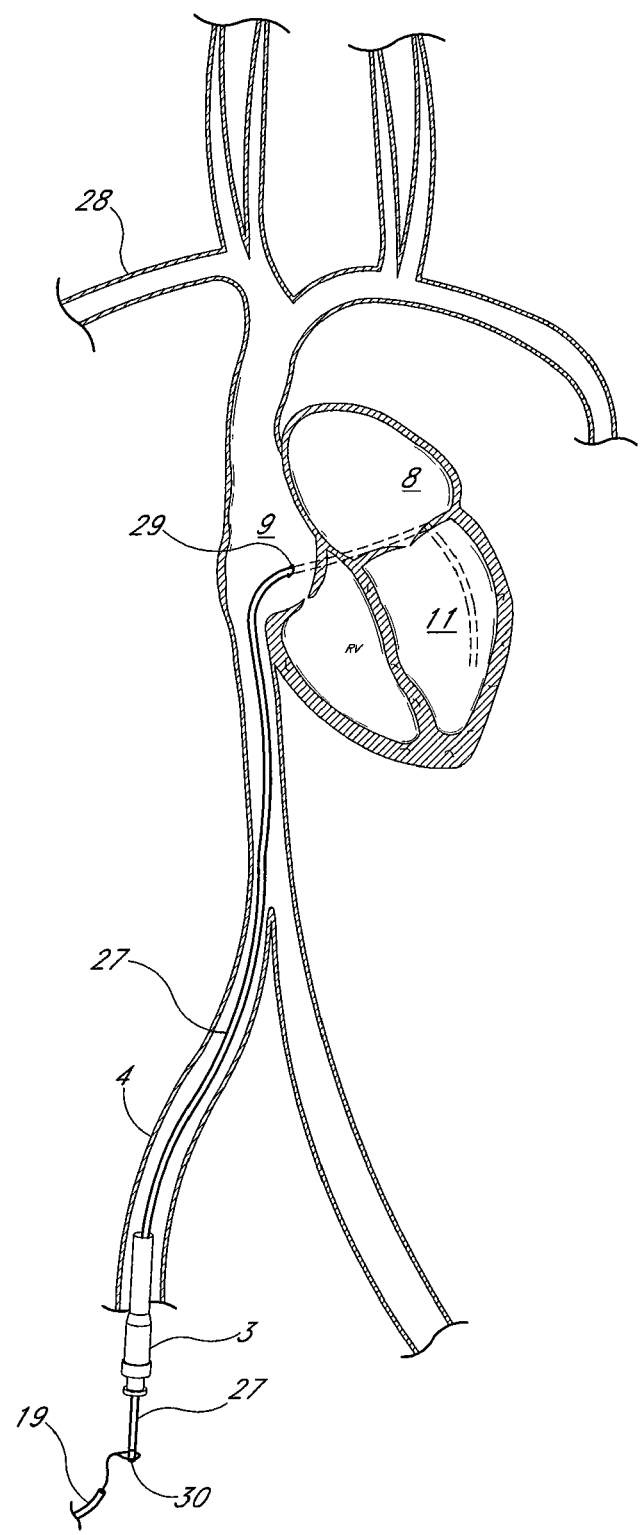
Figure 11D:
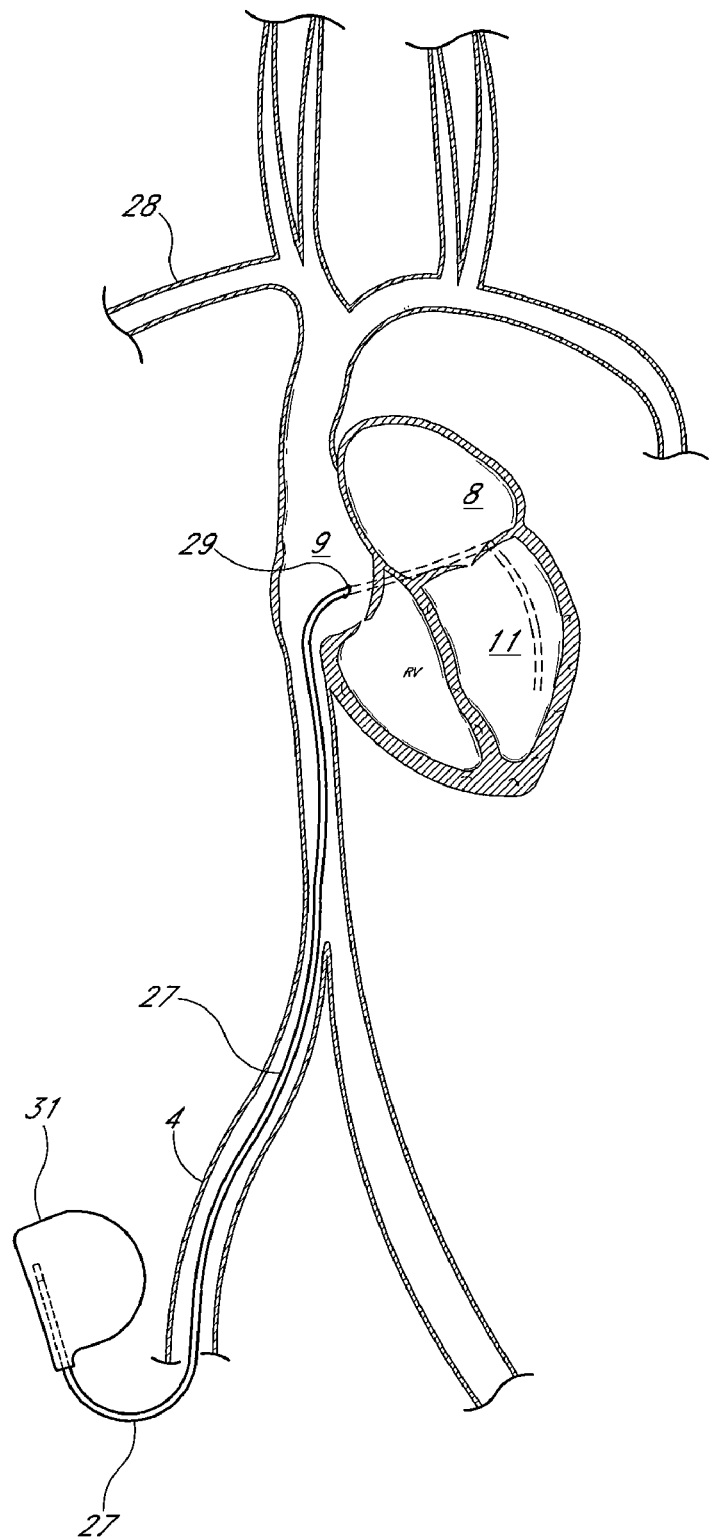

Alternatively, as demonstrated in FIG. 11B, if the lead 27 lacks sufficient length to be backloaded into the catheter and to exit from the second insertion site, or the lead connector 30 cannot fit through the catheter lumen, a snare 19 may be inserted from the second insertion site to the first insertion site. The snare 19, or any other device capable of releasably engaging the proximal end of the lead 27 may be used to pull the proximal end of lead 27 from the first insertion site to the second insertion site. FIG. 11C shows the snare 19 and the lead 27 withdrawn from the right femoral insertion site. The lead 27 is released from the snare 19 and connected to the biventricular pacemaker 31, as demonstrated in FIG. 11D.

In another embodiment, an extension device such as a guidewire or stylet is removably engaged to the proximal end of the lead 27 to allow the distal end of the lead to be advanced to its target location even when the length of the lead is shorter than the distance from the first insertion site to the target location. The proximal end of the extension device may then be transferred to a second insertion site that closer to the target site than the length of the lead, and the extension device may then be withdrawn so that the proximal end of the lead is externalized at the second insertion site. One example of this embodiment is the transfer of a short 45 cm left atrial pacing and/or pressure sensor lead inserted through a first insertion site in the femoral vein for transfer to a second insertion site in a subclavian vein. The first insertion site is more than 45 cm from the left atrium and will cause the proximal end of a lead to enter the body when the distal end of the lead is positioned at the target site. It will be clear to one skilled in the art that accessing the left atrium, via the atrial septum, may be easier and safer from the first insertion site, but that the ultimate desired location for the proximal end of the lead may be the subclavicular region. Furthermore, the skilled artisan will appreciate that it is undesirable to use a lead with sufficient length to span the entire distance from the femoral vein to the left atrium because once the lead is transferred to the second, closer, insertion site the excess length would have to be coiled and implanted within the patient.

Figure 12A:
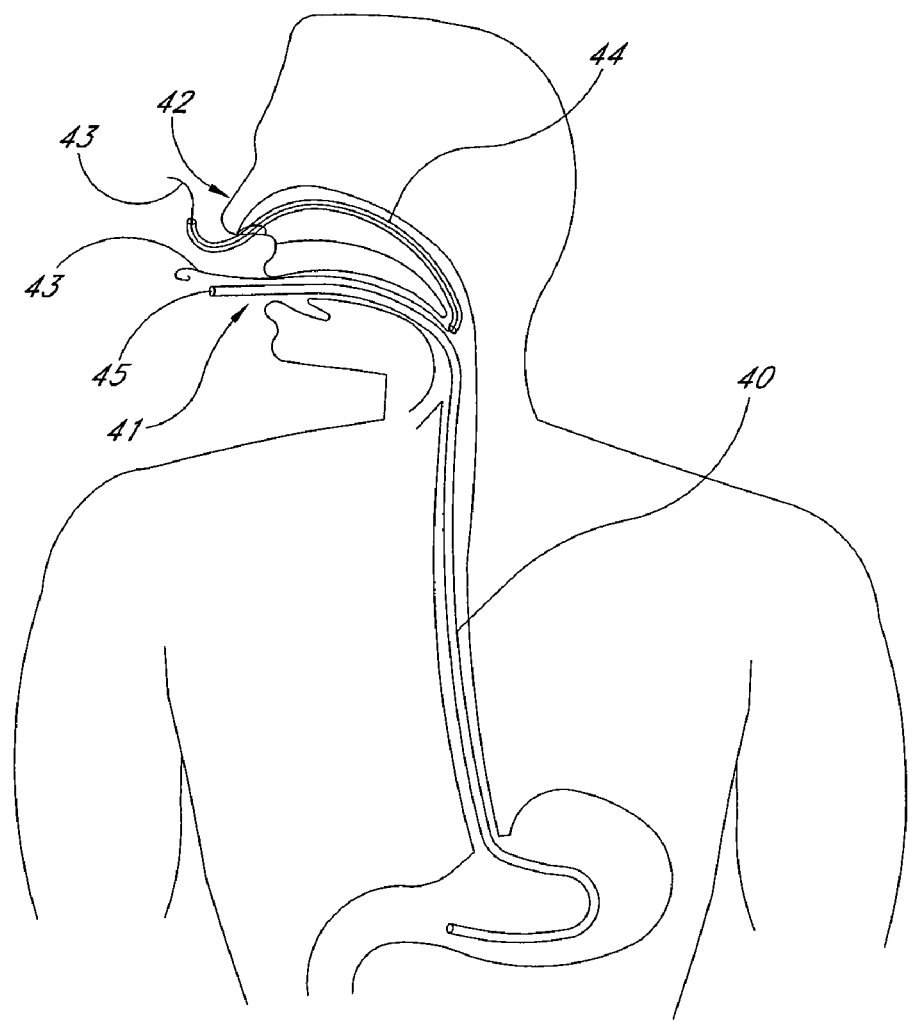
FIGS. 12A through 12C show the transfer of the proximal end of an orally-inserted gastric tube to a nasal insertion site.
Figure 12B:
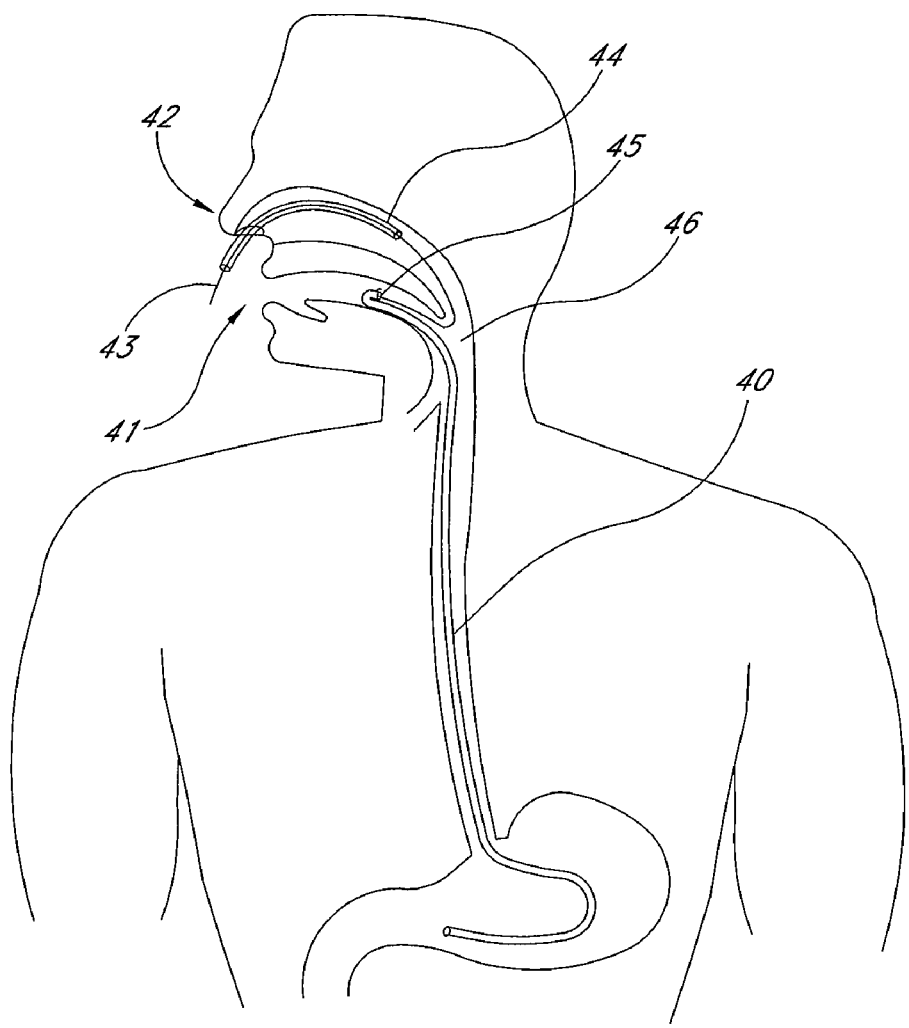
Figure 12C:
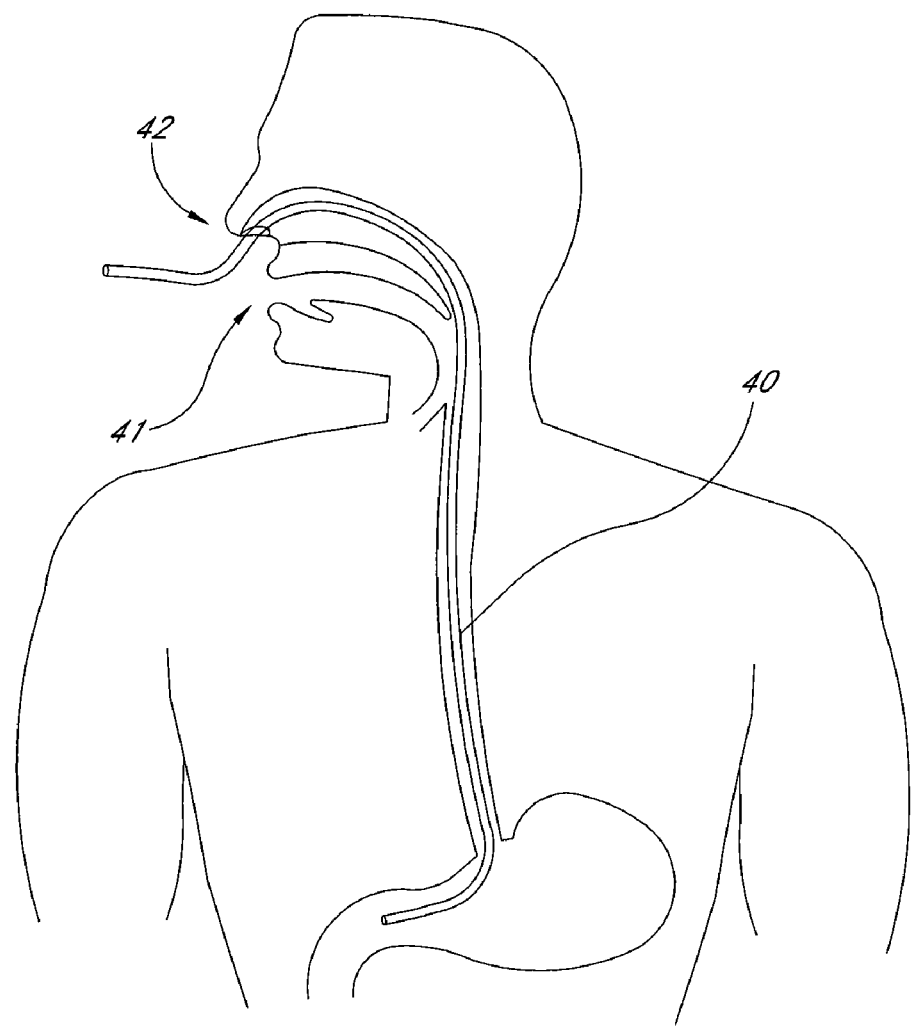

In another example, FIGS. 12A through 12C illustrate an embodiment of the invention adapted for the transfer of a gastric tube 40 from an oral first insertion site 41 to a nasal second insertion site 42. While an oral insertion site 41 is often a quicker and easier route for establishing a gastric 40 or endotracheal tube, a nasal insertion site 42 is usually more comfortable for the patient, particularly when the tube 40 must be left in place for extended periods of time, or when the patient is conscious. FIG. 12A shows the placement of a guidewire 43 from a second insertion site 42 through the nose, via a nasal sheath 44, to the first insertion site 41 in the mouth. In FIG. 12B, the distal end of the guidewire 43 is connected to the proximal end 45 of the gastric tube 40, and the guidewire 43 is withdrawn through the nasal sheath 44, pulling the proximal end of the gastric tube 40 back into the throat 46.

FIG. 12C shows the final configuration of the gastric tube 40 after the complete withdrawal of the guidewire 43 and the nasal sheath 44, completing the transfer of the gastric tube insertion site from the mouth to the nose.

In another embodiment, the method of manipulating insertion pathways for accessing target sites further comprises providing a kit, or system, for performing the guidewire and/or medical device transfer. In one embodiment, the kit, or system, is a combination, assemblage and/or compilation of materials suitable for a common purpose and comprises an introducer sheath for each insertion site, a torqueable catheter and two guidewires. In another embodiment, the kit further comprises at least one of the guidewires having a coilable soft curled tip. In another embodiment, the kit further comprises at least one of the guidewires having a movable inner core mandrel. In another embodiment, the kit or system further comprises a snare. In another embodiment, the kit further comprises a thin-walled introducer. In a further embodiment, the kit includes a Brockenbrough needle catheter. In yet another embodiment, the kit further includes a Mullins sheath.

In another embodiment of the invention, a guidewire for manipulating insertion pathways to access target sites in the body is provided. In one embodiment of the invention, the guidewire 10 has a length of about 150 cm to about 350 cm, preferably between about 180 cm to about 280 cm, more preferably between about 220 cm to about 250 cm. In one embodiment, the guidewire 10 has an outer diameter of about 0.010 to about 0.064 inches. The outer diameter of the guidewire 10 need not be uniform throughout the length of the guidewire. In one embodiment, the distal portion 12 of the guidewire 10 may have a reduced diameter to facilitate insertion of the guidewire 10 into body structures or catheters. In another embodiment, changes to the diameter of the guidewire 10 along the length of the guidewire may also be used alter the stiffness and flexibility along those portions. The guidewire 10 may be configured with a blunt distal end 34 for reducing the risk of damaging tissue during manipulation of the guidewire 10. In another embodiment, the guidewire 10 features at least one radio-opaque marker (not shown) along the length of the guidewire to provide visualization of the guidewire under radiography or fluoroscopy.

Guidewires may be configured as single piece or multi-piece constructions. In one embodiment, the guidewire has a single-piece construction and comprises a tapered core mandrel with a stiffer proximal end and a flexible, shaped distal end. Such wires are often coated with a hydrophilic substance that increases lubricity on contract with blood. One example of this type of wire construction is the Glidewire by Turumo of Japan. This type of wire is particularly useful for advancing through blood vessels that are blocked by thrombus or atherosclerosis.

In one embodiment, the guidewire has a multi-piece construction comprising a moveable inner core and an outer helical wound coil, with an opening at its proximal end and a closed-off distal end, creating a closed-tip lumen for the moveable core. In another embodiment, the distal tip is open-ended and the guidewire has a through-lumen that may be used for injecting or withdrawing diagnostic or therapeutic substances. The distal end of the coil may be preshaped into a "J", "hockey-stick" or other configuration, or may contain a deformable inner strip or a shaping ribbon that allows the operator to create a desired tip configuration. In one embodiment, the core provides variable stiffness to at least a portion of the guidewire body. In one embodiment, the distal tip of the core may be tapered to create a smooth transition from the stiff portion to the flexible portion of the guidewire. In another embodiment, the tip may be rounded to improve passage of the core through the coil. In yet another embodiment, movement of the core may be facilitated with lubrication such as silicone oil or a polymeric coating. In one embodiment, the outer coil may be coated or bonded with a material such as Teflon to alter lubricity and/or an anticoagulant such as heparin. In one embodiment, the distal end of the core is capable of forming a friction fit or a mechanical interfit with the distal end of the coil with respect to rotation and facilitate the transmission of torque applied at the proximal core to the distal tip. This allows the user to alter the orientation of the distal tip and allow selection of vessels or other lumens as the wire is advanced and "torqued." Moveable core guidewires may be advantageously used to position catheters in the body through a tortuous path while reducing trauma to body structures.

In another example of multi-piece construction, the core is fixed to a distal flexible coil that covers the distal tapered portion of the core transitioning into a shapeable tip. In one embodiment, such guidewires provide improved torque control. In another embodiment, the guidewire has a radio-opaque plating (such as a platinum or gold plating) applied to at least the distal end of the coil to aid in fluoroscopic visualization. In one embodiment, up to about 15 cm of the distal end is rendered radio-opaque. In a preferred embodiment, the distal 2 cm to 10 cm end of the coil is radio-opaque. These wires are used to selectively steer into small branches and provide a trackable path for interventional devices such as balloons or stents. Another variant of this type of construction is the wire described by Inoue as manufactured by the Toray Corporation of Japan. This wire has about a 0.025" outer diameter stainless steel mandrel that tapers, with the distal portion covered by a flexible coil and configured in a spiral shape. This wire is particularly useful for securing a stable position in the left atrium after transseptal catheterization.

Figure 13A:
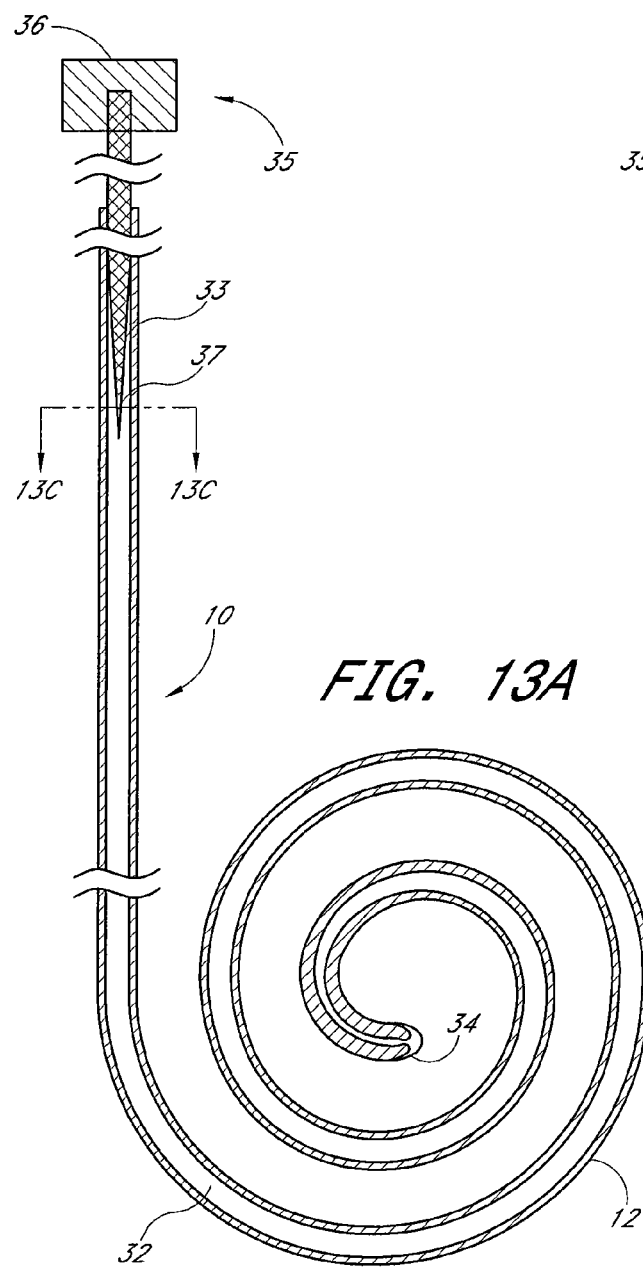
FIGS. 13A through 13C detail one embodiment of the invention comprising a guidewire with a movable core mandrel.
Figure 13B:
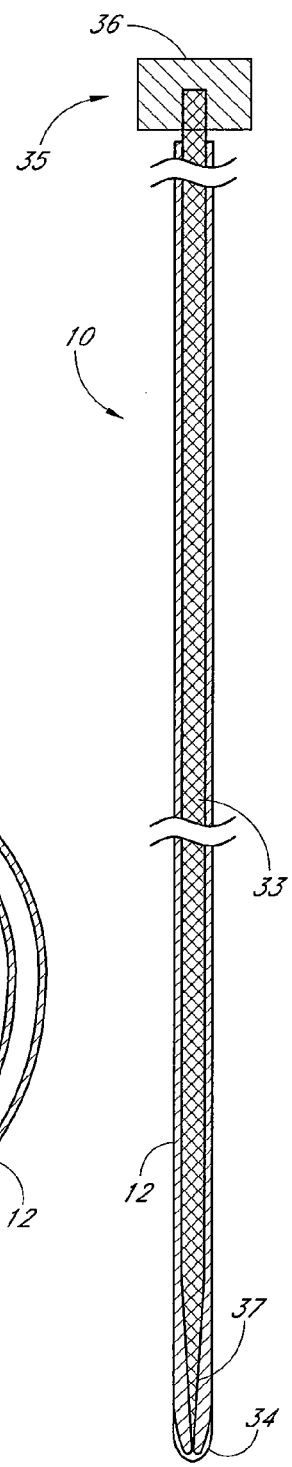
Figure 13C:
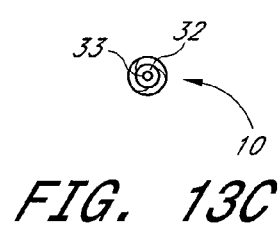

As shown in FIGS. 13A through 13C, in one embodiment, the guidewire 10 has an internal lumen 32. In one embodiment, the lumen 32 extends generally throughout the length of the guidewire. In another embodiment, the lumen 32 extends generally from about 10% to about 99% of the length of the guidewire. In still another embodiment, the lumen 32 generally extends about 95% of the guidewire length from the proximal end of the guidewire 10. In one embodiment, the lumen 32 has an internal diameter between about 0.012 inches to about 0.045 inches, preferably between about 0.020 inches to about 0.030 inches, and more preferably between about 0.020 inches to 0.025 inches. In one embodiment, the internal lumen 32 contains a core mandrel 33, shaft, and/or device for facilitating insertion and steerability of the guidewire 10. The core mandrel 33 has an outer diameter between about 0.012 inches to about 0.045 inches, preferably between about 0.020 inches to about 0.030 inches, and more preferably between about 0.020 to 0.025 inches. The core mandrel 33 has a length between about 20% to about 200% of the guidewire 10 length, preferably between about 50% to about 120%, and more preferably about 110%. The core mandrel may be moveable, removable, fixed or a combination thereof. By adjusting the position of a moveable or removable mandrel 33 within the guidewire 10, the stiffness of the guidewire may be adjusted by the user. In one embodiment, increased stiffness of the guidewire 10 may improve the steerability of the guidewire 10 to the target site and provide increased column strength to pass a device over the guidewire 10 without deforming the guidewire 10 and changing the insertion pathway or dislodging the distal portion of the guidewire 10 from the target site. By removing the mandrel 33, the flexibility of the guidewire 10 is increased to allow passage through tortuous routes in the body. In some embodiments of the invention, the distal portion 12 of the guidewire 10 is capable of coiling or assuming a preconfigured shape when the mandrel 33 is in the retracted position. In one embodiment, the distal portion 12 of the guidewire 10 forms a J-shape when the mandrel 33 is in the retracted position. In another embodiment, the guidewire 10 forms a coil shape. One skilled in the art will understand that the distal portion 12 of the guidewire 10 can be configured to provide steerability to and anchoring at any of a variety of target sites in the body, including but not limited to, the right atrium, left atrium, coronary sinus, pulmonary artery, left ventricle, aorta, stomach, duodenum, gallbladder, pancreas, renal calyxes, ureters, bladder and nasopharynx. In one embodiment, shown for example in FIG. 13A, the mandrel 33 is shown in a partially retracted position to allow flexibility in the distal portion 12 of the guidewire 10 and allows the inherent bias in the distal portion 12, if any, to assume a preconfigured shape, such as a coil or J-shape. In FIG. 13B, the mandrel 33 is in a fully extended position to generally stiffen the entire length of the guidewire 10 and to overcome at least some of the inherent bias of the distal portion 12 and at least partially straighten the distal portion 12. The mandrel 33 is capable of partial retraction and extension to vary the extent of the guidewire stiffening.

Figure 14A:
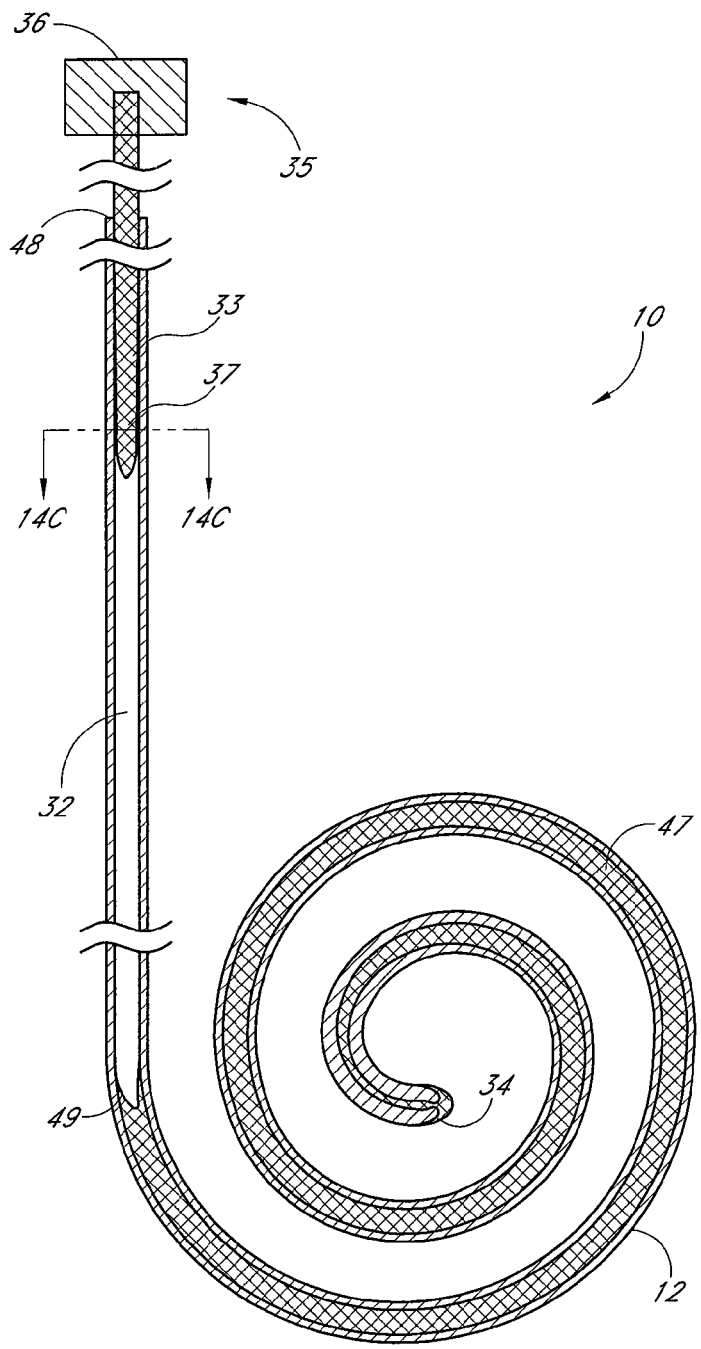
FIGS. 14A through 14C detail one embodiment of the invention comprising a guidewire with a proximal movable core mandrel and a fixed distal core.
Figure 14C:
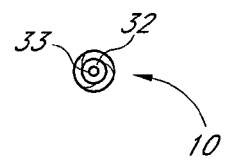
Figure 14B:
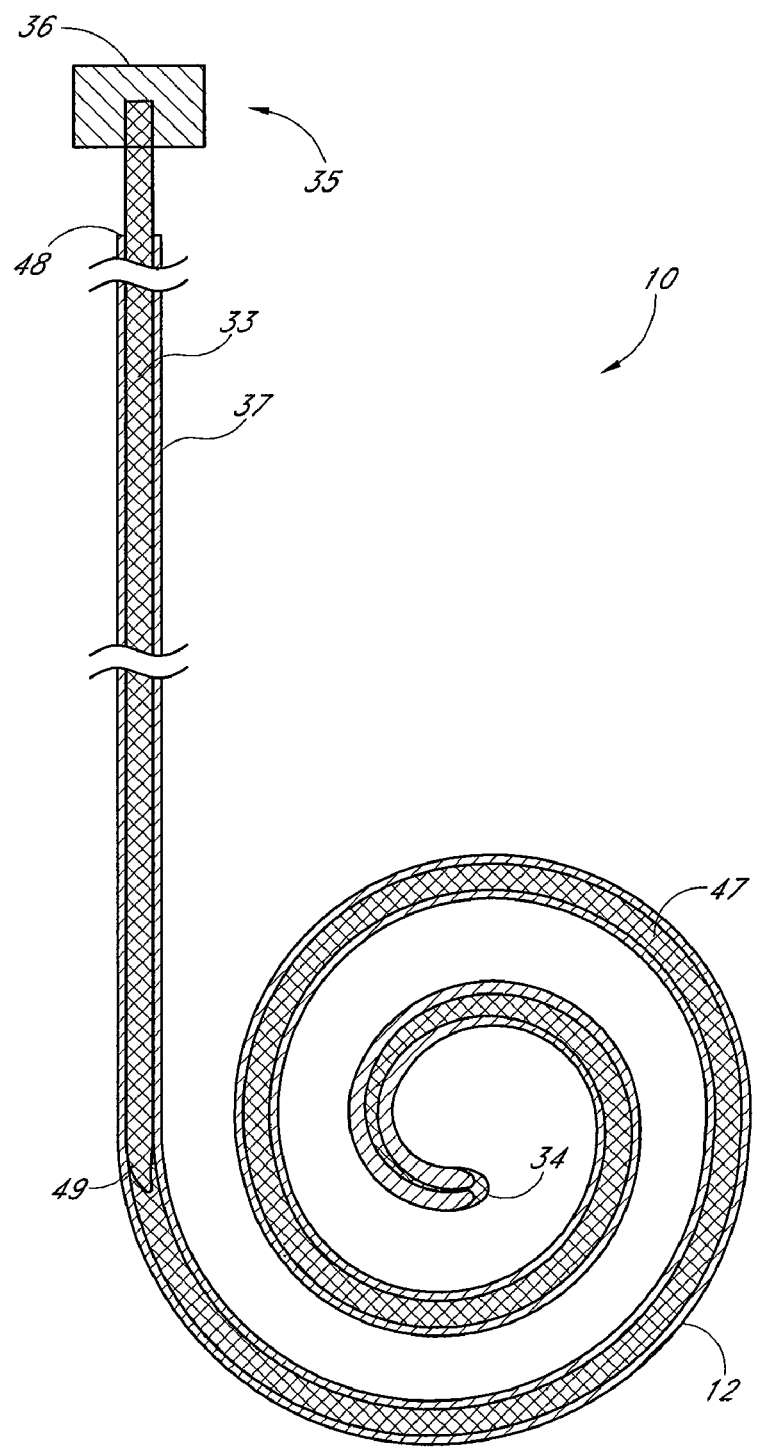

FIGS. 14A to 14C show another embodiment of the guidewire 10 comprising a distal fixed core 47 and a guidewire lumen 32 with moveable or removable core 33. In one embodiment, the guidewire lumen 32 has a proximal open end 48 and a closed distal end 49, with a length that is generally less than the full length of the guidewire 10. Preferably, the distal end 49 of the guidewire lumen 32 is positioned generally in the portion of the guidewire that transitions from the proximal straight portion to the preshaped distal portion 12. In one embodiment, the fixed distal core advantageously maintains the stiffness of preshaped distal portion 12 for anchoring the distal guidewire in the desired position, while the moveable core enhances flexibility during the repositioning of the proximal portion of the guidewire 10. In one embodiment, the distal fixed core comprises a stiff radio-opaque material, such as a platinum or gold alloy.

In one embodiment, the movable core mandrel 33 has a proximal end 35 with a tab 36 or other type of handle to facilitate manipulation of the mandrel 33. In another embodiment, the mandrel 33 lacks a tab 36 so that a device can be passed over guidewire 10 without having to remove mandrel 33. The movable core mandrel 33 may have a tapered distal end 37 to facilitate insertion and extension of the mandrel 33 through the internal lumen 32 of the guidewire 10. In one embodiment, the mandrel 33 is made from stainless steel or nickel titanium alloy (nitinol). One skilled in the art will understand that the material and structure selected for the mandrel 33 can be based upon the desired stiffness, ductility, elastic deformation and other characteristics desired.

In one embodiment, the guidewire 10 is flexible or deformable, and the mandrel 33 is more rigid. In another embodiment, the mandrel 33 is flexible or deformable, and the guidewire 10 is more rigid. In one embodiment, the more rigid guidewire 10 comprises an opening at the distal end so that it can be passed over the proximal end of the mandrel and into the target site.

In one embodiment, the guidewire 10 is uniformly flexible along its length. In another embodiment, the pliancy of the guidewire 10 is not uniform throughout the length of the guidewire 10, even when the mandrel 33 is completely removed from the internal lumen 32. In a preferred embodiment, the middle portion of the guidewire 10 is more flexible than the distal end and/or the proximal end of the guidewire 10. One advantage of this alternating flexibility is that it facilitates bending and/or sharp turns in the body lumen.

In one embodiment, the guidewire comprises a material and structure with sufficient ductility capable of withstanding deformation of at least about 180 degrees to about 540 degrees of bending within a body or sheath lumen without breakage. In another embodiment, the guidewire comprises a material and structure with sufficient ductility and a yield point capable of withstanding deformation of at least about 220 degrees in a body or sheath lumen without breakage or plastic deformation. The guidewire may be made in whole or in part from a material selected from one or more of the following: stainless steel alloys such as NP35-N, nickel titanium (nitinol), tantalum, or a combination thereof. Similarly, the guidewire may be constructed from polymeric or composite materials including but not limited to polyethylenes, polyurethanes, carbon fibers, or blended combinations thereof. In another embodiment, the guidewire may be constructed of a combination of metallic and polymeric/composite materials. In another embodiment, the guidewire is coated with a hydrophilic coating or a polymer such as ePTFE to facilitate the passage of the guidewire through the body. One skilled in the art can select the guidewire material and structure to provide the desired characteristics, including but not limited to torqueability, stiffness, ductility, friction coefficient, radio-opacity and deformation characteristics.

While this invention has been particularly shown and described with references to embodiments thereof, it will be understood by those skilled in the art that various changes in form and details may be made therein without departing from the scope of the invention. For all of the embodiments described above, the steps of the methods need not be performed sequentially.

What is claimed is:

1. A method of transferring a guidewire from one insertion site to another insertion site, comprising:
   introducing a first guidewire to a femoral access site, wherein said first guidewire has a proximal and a distal end;
   introducing the distal end of said first guidewire to a target site;
   introducing a catheter having a proximal end and a distal end from a subclavian access site and advancing the distal end to a proximity of said femoral access site;
   introducing a second guidewire, wherein said second guidewire has a proximal and a distal end, through the proximal end of said catheter such that the distal end of said second guidewire extends out through said femoral access site;
   emerging the distal end of said catheter through said femoral access site by advancing said catheter over said second guidewire; and
   exiting the proximal end of said first guidewire through the proximal end of the catheter at the subclavian access site by removing said second guidewire entirely from said catheter and inserting the proximal end of said first guidewire into the distal end of said catheter.

2. The method of claim 1, further comprising:
   snaring the distal end of said second guidewire with a snare; and
   pulling said snare and the distal end of said second guidewire out from said femoral access site.

3. The method of claim 1, further comprising placing an introducer at said femoral access site.

4. The method of claim 1, further comprising placing an introducer at said subclavian access site.

5. The method of claim 1, wherein the step of introducing the distal end of said first guidewire to a target site comprises introducing the distal end of said first guidewire to a site in a left atrium.

6. The method of claim 1, wherein the step of introducing a catheter having a proximal end and a distal end over said second guidewire from said subclavian access site to said femoral access site comprises introducing a catheter having a proximal end and a distal end over said second guidewire from said subclavian access site to a right femoral vein.

7. The method of claim 1, wherein the step of introducing a catheter having a proximal end and a distal end over said second guidewire from said subclavian access site to said femoral access site comprises introducing a catheter having a proximal end and a distal end over said second guidewire from a left subclavian vein to said femoral access site.

8. A method of transferring a guidewire from a femoral access site to a subclavian access site, comprising:
   introducing a first guidewire to the femoral access site, wherein the first guidewire has a proximal and a distal end;
   introducing the distal end of the first guidewire to a chamber of a heart;
   introducing a catheter having a proximal end and a distal end from the subclavian access site and advancing the distal end to a proximity of the femoral access site;
   introducing a second guidewire, wherein the second guidewire has a proximal and a distal end, through the proximal end of the catheter such that the distal end of the second guidewire extends out through the femoral access site;
   emerging the distal end of the catheter through the femoral access site by advancing the catheter over the second guidewire; and
   exiting the proximal end of the first guidewire through the proximal end of the catheter at the subclavian access site by removing the second guidewire entirely from the catheter and inserting the proximal end of the first guidewire into the distal end of the catheter.

9. The method of claim 8, further comprising:
   snaring the distal end of the second guidewire with a snare; and
   pulling the snare and the distal end of the second guidewire out from the femoral access site.

10. The method of claim 8, further comprising placing an introducer at the femoral access site.

11. The method of claim 8, further comprising placing an introducer at the subclavian insertion site.

12. The method of claim 8, wherein the step of introducing the distal end of the first guidewire to a chamber of a heart comprises introducing the distal end of the first guidewire to a site in a left atrium.

13. The method of claim 8, wherein the step of introducing the distal end of the first guidewire to a chamber of a heart comprises introducing the distal end of the first guidewire to a site in the right ventricle.

* * * * *